US008815826B2

(12) United States Patent  (10) Patent No.: US 8,815,826 B2
Chau  (45) Date of Patent: Aug. 26, 2014

(54) TARGETING MICRORNAS FOR THE TREATMENT OF FIBROSIS

(75) Inventor: B. Nelson Chau, San Diego, CA (US)

(73) Assignee: Regulus Therapeutics, Inc., San Diego, CA (US)

( * ) Notice: Subject to any disclaimer, the term of this patent is extended or adjusted under 35 U.S.C. 154(b) by 0 days.

(21) Appl. No.: 13/811,423

(22) PCT Filed: Jul. 22, 2011

(86) PCT No.: PCT/US2011/045007
§ 371 (c)(1),
(2), (4) Date: Mar. 22, 2013

(87) PCT Pub. No.: WO2012/012716
PCT Pub. Date: Jan. 26, 2012

(65) Prior Publication Data
US 2013/0184217 A1  Jul. 18, 2013

Related U.S. Application Data

(60) Provisional application No. 61/367,034, filed on Jul. 23, 2010, provisional application No. 61/419,148, filed on Dec. 2, 2010.

(51) Int. Cl.
*A61K 48/00* (2006.01)
*C07H 21/02* (2006.01)
*C07H 21/04* (2006.01)

(52) U.S. Cl.
USPC ........ 514/44; 536/23.1; 536/24.3; 536/24.31; 536/24.33; 536/24.5

(58) Field of Classification Search
CPC . C12N 15/113; C12N 2310/113; A61K 45/06
See application file for complete search history.

(56) References Cited

FOREIGN PATENT DOCUMENTS

| EP | 2305810 | 4/2011 |
|---|---|---|
| WO | 2005/013901 | 2/2005 |
| WO | 2005/054494 | 6/2005 |
| WO | 2005078139 A2 | 8/2005 |
| WO | 2005/118806 | 12/2005 |
| WO | 2006/137941 | 12/2006 |
| WO | 2007/027775 | 3/2007 |
| WO | 2007/112754 | 10/2007 |
| WO | 2008/043521 | 4/2008 |
| WO | 2009/018493 | 2/2009 |
| WO | 2009/043353 | 4/2009 |
| WO | 2009/106367 | 9/2009 |
| WO | 2009/109665 | 9/2009 |
| WO | 2010/056737 | 5/2010 |
| WO | 2010/135570 | 11/2010 |
| WO | 2010/151640 | 12/2010 |
| WO | 2011/126842 | 10/2011 |
| WO | 2012/012716 | 1/2012 |

OTHER PUBLICATIONS

Krutzfeldt et al. (Nature 2005, vol. 438, 685-689).*
Fei et al. (Journal of Drug Targeting, 2008, 16(9), 688-693).*
Dean et al. (Journal of Histochemistry & Cytochemistry, vol. 53(10), 2005, 1245-1256).*
Boyer et al., "Rearrangements of desmosomal and cytoskeletal proteins during the transition from epithelial to fibroblastoid organization in cultured rat bladder carcinoma cells," J. Cell. Biol, 1989, 109: 1495-1509.
Chan et al., "Role of microRNA-214 in ginsenoside-Rg1-induced angiogenesis," Eur J Pharm Sci., 2009, 38 (4):370-377.
Chilosi et al., "Aberrant Wnt/beta-catenin pathway activation in idiopathic pulmonary fibrosis,". Am. J. Pathol., 2003, 162: 1495-502.
Flynt et al., "Zebrafish miR-214 modulates Hedgehog signaling to specify muscle cell fate," Nat Genet, 2007, 39 (2):259-263.
Godwin et al., "Identification of a microRNA signature of renal ischemia reperfusion injury.," Proc Natl Acad Sci USA. 2010 , 107(32):14339-44.
Greenburg et al., "Cytodifferentiation and tissue phenotype change during transformation of embryonic lens epithelium to mesenchyme-like cells in vitro," Dev. Biol., 1986, 115: 363-379.
Ikeda et al., "Altered microRNA expression in human heart disease," Physiol Genomics, 2007, 31:367-373.
Ikegami et al., "Liver fibrosis: possible involvement of EMT," Cells Tissues Organs, 2007, 185: 213-221.
Iwano et al., "Evidence that fibroblasts derive from epithelium during tissue fibrosis," J. Clin. Invest, 2002, 110: 341-50.
Jiang et al., "MicroRNAs and the regulation of fibrosis," FEBS Journal, 2010, 277:2015-2021.
Kalluri et al., "Epithelial-mesenchymal transition and its implications for fibrosis," J. Clin. Invest, 2003, 112: 1776-1784.
Kida et al., "Twist relates to tubular epithelial-mesenchymal transition and interstitial fibrogenesis in the obstructed kidney," J Histochem Cytochem, 2007, 55:661-673.
Lee et al., "Twist-1 regulates the miR-199a/214 cluster during development," Nucleic Acid Res, 2009, 37(1):123-128.
Li et al. "Role of microRNA-214-targeting phosphatase and tensin homolog in advanced glycation end product-induced apoptosis delay in monocytes," J Immunol. 2011, 186(4):2552-60.
Liu et al., "MicroRNA-214 promotes myogenic differentiation by facilitating exit from mitosis via down-regulation of proto-oncogene N-ras," J Biol Chem, 2010, 284(34):26599-26607.
Pandit et al., "Inhibition and role of let-7d in idiopathic pulmonary fibrosis," Am J Respir Crit Care Med, 2010, 182 (2):220-9.
Penna et al., "microRNA-214 contributes to melanoma tumour progression through suppression of TFAP2C," EMBO J, 2011, 30(10):1990-2007.
Pozharskaya et al., "Twist: a regulator of epithelial-mesenchymal transition in lung fibrosis," PLoS One, 2009, 4 (10):e7559.
Saal et al., "MicroRNAs and the kidney: coming of age," Curr Opin Nephrol Hypertens, 2009, 18:317-323.
Santhakumar et al., "Combined agonist-antagonist genome-wide functional screening identifies broadly active antiviral microRNAs," PNAS, 2010, 107(31):13830-13835.
Sempowski, et al., "Fibroblast heterogeneity in the healing wound," Wound Repair Regeneration, 1995, 3: 120-131.
Strutz et al., "Identification and characterization of a fibroblast marker: FSP1," J. Cell. Biol, 1995, 30: 393-405.
Uehara et al., "Expression of a human hepatocyte growth factor/scatter factor cDNA in MDCK epithelial cells influences cell morphology, motility, and anchorage-independent growth," J. Cell. Biol, 1992, 117: 889-894.

(Continued)

*Primary Examiner* — Amy Bowman
(74) *Attorney, Agent, or Firm* — Casimir Jones, S.C.

(57) ABSTRACT

Provided herein are compositions and methods for the modulation of 'miR-214 for the treatment and/of prevention of fibrosis and fibroproliferative conditions.

14 Claims, 1 Drawing Sheet

(56) References Cited

OTHER PUBLICATIONS

Van Rooij et al., "A signature pattern of stress-responsive microRNAs that can evoke cardiac hypertrophy and heart failure," Proc Natl Acad Sci USA. 2006, 103(48):18255-60.

Van Rooij et al., "Dysregulation of microRNAs after myocardial infarction reveals a role of miR-29 in cardiac fibrosis," PNAS, 2008, 105(35):13027-13032.

International Search Report and Written Opinion, mailed Mar. 27, 2012, for PCT/US2011/045007 (21 pages).

International Preliminary Report on Patentability, mailed Jan. 23, 2013, for PCT/US2011/045007 (12 pages).

Aurora et al., "MicroRNA-214 protects the mouse heart from ischemic injury by controlling Ca2+ overload and cell death," The Journal of Clinical Investigation, 2012, 122(4):1222-1232.

Denby et al., "miR-21 and miR-214 Are Consistently Modulated during Renal Injury in Rodent Models," Am J Pathol., 2011, 179(2):661-672.

Denby et al., "MicroRNA-214 Antagonism Protects against Renal Fibrosis," Journal of the American Society of Nephrology, 2014, 25:1-16.

Maubach et al., "miRNA studies in in vitro and in vivo activated hepatic stellate cells," World Journal of Gastroenterology, 2011, 17(22):2748-2773.

Ogawa et al., "MicroRNA-221/222 upregulation indicates the activation of stellate cells and the progression of liver fibrosis," Gut, 2012, 61:1600-1609.

\* cited by examiner

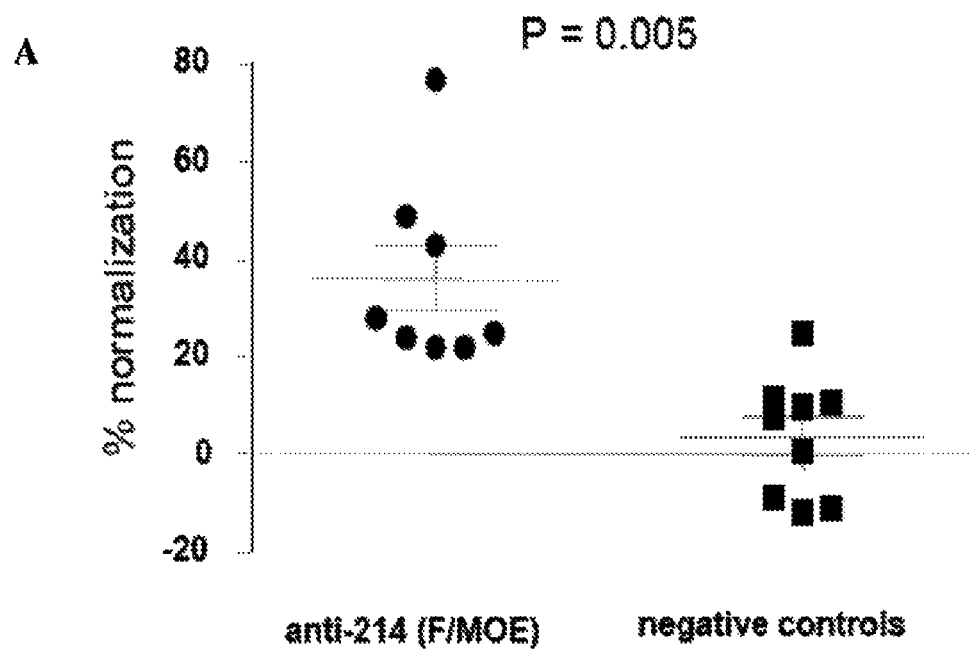
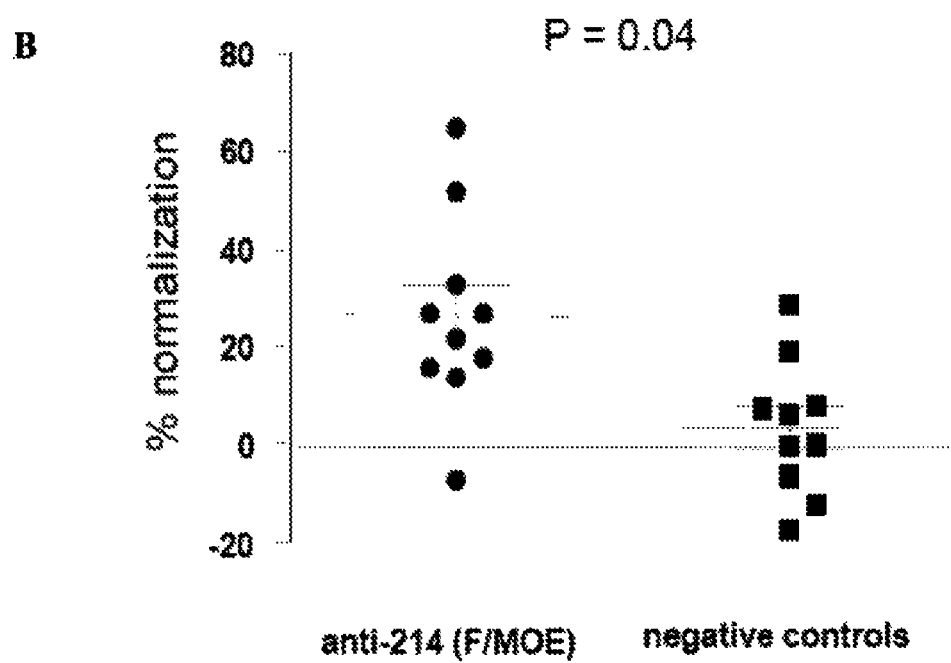

SEQUENCE LISTING

```
<160> NUMBER OF SEQ ID NOS: 31

<210> SEQ ID NO 1
<211> LENGTH: 22
<212> TYPE: RNA
<213> ORGANISM: Homo sapiens
<220> FEATURE:
<221> NAME/KEY: misc_feature
<223> OTHER INFORMATION: microRNA sequence

<400> SEQUENCE: 1
acagcaggca cagacaggca gu                                              22

<210> SEQ ID NO 2
<211> LENGTH: 110
<212> TYPE: RNA
<213> ORGANISM: Homo sapiens
<220> FEATURE:
<221> NAME/KEY: misc_feature
<223> OTHER INFORMATION: Stem-loop sequence

<400> SEQUENCE: 2
ggccuggcug gacagaguug ucaugugucu gccugucuac acuugcugug cagaacaucc     60
gcucaccugu acagcaggca cagacaggca gucacaugac aacccagccu                110

<210> SEQ ID NO 3
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 3
actgcctgtc tgtgcctgct gt                                              22

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide
```

```
<400> SEQUENCE: 4
ctgcctgtct gtgcctgctg t                                            21

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
tgcctgtctg tgcctgctgt                                              20

<210> SEQ ID NO 6
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 6
gcctgtctgt gcctgctgt                                               19

<210> SEQ ID NO 7
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 7
cctgtctgtg cctgctgt                                                18

<210> SEQ ID NO 8
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 8
ctgtctgtgc ctgctgt                                                 17

<210> SEQ ID NO 9
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 9
tgtctgtgcc tgctgt                                                  16

<210> SEQ ID NO 10
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 10
gtctgtgcct gctgt                                                   15

<210> SEQ ID NO 11
<211> LENGTH: 14
```

```
<212> TYPE: DNA
<213> ORGANISM: Artificial Sequence
<220> FEATURE:
<223> OTHER INFORMATION: Synthetic oligonucleotide

<400> SEQUENCE: 11
tctgtgcctg ctgt                                                        14

<210> SEQ ID NO 12
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 12
ctgtgcctgc tgt                                                         13

<210> SEQ ID NO 13
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 13
tgtgcctgct gt                                                          12

<210> SEQ ID NO 14
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 14
gtgcctgctg t                                                           11

<210> SEQ ID NO 15
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 15
tgcctgctgt                                                             10

<210> SEQ ID NO 16
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 16 gcctgctgt                                                               9

<210> SEQ ID NO 17
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 17
```

-continued cctgctgt    8

<210> SEQ ID NO 18
<211> LENGTH: 7
<212> TYPE: DNA
<213> ORGANISM: Artificial Sequence
<220> FEATURE:
<223> OTHER INFORMATION: Synthetic oligonucleotide

<400> SEQUENCE: 18 ctgctgt    7

<210> SEQ ID NO 19
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 19 acagca    6

<210> SEQ ID NO 20
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 20 cagcag    6

<210> SEQ ID NO 21
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 21 agcagg    6

<210> SEQ ID NO 22
<211> LENGTH: 7
<212> TYPE: DNA
<213> ORGANISM: Artificial Sequence
<220> FEATURE:
<223> OTHER INFORMATION: Synthetic oligonucleotide

<400> SEQUENCE: 22 acagcag    7

<210> SEQ ID NO 23
<211> LENGTH: 7
<212> TYPE: DNA
<213> ORGANISM: Artificial Sequence
<220> FEATURE:
<223> OTHER INFORMATION: Synthetic oligonucleotide

<400> SEQUENCE: 23 cagcagg    7

<210> SEQ ID NO 24
<211> LENGTH: 8
<212> TYPE: DNA
<213> ORGANISM: Artificial Sequence

```
<220> FEATURE:
<223> OTHER INFORMATION: Synthetic oligonucleotide

<400> SEQUENCE: 24 acagcagg                                                                    8

<210> SEQ ID NO 25
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 25 cagcaggc                                                                    8

<210> SEQ ID NO 26
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 26 tgctgt                                                                      6

<210> SEQ ID NO 27
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 27 ctgctg                                                                      6

<210> SEQ ID NO 28
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 28 cctgct                                                                      6

<210> SEQ ID NO 29
<211> LENGTH: 7
<212> TYPE: DNA
<213> ORGANISM: Artificial Sequence
<220> FEATURE:
<223> OTHER INFORMATION: Synthetic oligonucleotide

<400> SEQUENCE: 29 cctgctg                                                                     7

<210> SEQ ID NO 30
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 30 gcctgctg                                                                    8
```

```
<210> SEQ ID NO 31
<211> LENGTH: 72
<212> TYPE: RNA
<213> ORGANISM: Homo sapiens

<400> SEQUENCE: 31
ugucggguag cuuaucagac ugauguugac uguugaaucu cauggcaaca ccagucgaug      60
ggcugucuga ca                                                         72
```

TARGETING MICRORNAS FOR THE TREATMENT OF FIBROSIS

This application claims the benefit of U.S. Provisional Application No. 61/367,034, filed Jul. 23, 2010, and U.S. Provisional Application No. 61/419,148, filed Dec. 2, 2010, both of which are incorporated by reference herein in their entireties for any purpose.

FIELD OF INVENTION

Provided herein are methods and compositions for the treatment of fibrosis and fibroproliferative disorders.

DESCRIPTION OF RELATED ART

MicroRNAs (miRNAs), also known as "mature miRNA" are small (approximately 18-24 nucleotides in length), non-coding RNA molecules encoded in the genomes of plants and animals. In certain instances, highly conserved, endogenously expressed miRNAs regulate the expression of genes by binding to the 3'-untranslated regions (3'-UTR) of specific mRNAs. More than 1000 different miRNAs have been identified in plants and animals. Certain mature miRNAs appear to originate from long endogenous primary miRNA transcripts (also known as pri-miRNAs, pri-mirs, pri-miRs or pri-pre-miRNAs) that are often hundreds of nucleotides in length (Lee, et al., EMBO J., 2002, 21(17), 4663-4670).

Functional analyses of miRNAs have revealed that these small non-coding RNAs contribute to different physiological processes in animals, including developmental timing, organogenesis, differentiation, patterning, embryogenesis, growth control and programmed cell death. Examples of particular processes in which miRNAs participate include stem cell differentiation, neurogenesis, angiogenesis, hematopoiesis, and exocytosis (reviewed by Alvarez-Garcia and Miska, Development, 2005, 132, 4653-4662).

SUMMARY OF INVENTION

Provided herein are methods for the treatment of fibrosis. Such methods comprise administering to a subject having fibrosis a compound comprising a modified oligonucleotide consisting of 8 to 25 linked nucleosides, and having a nucleobase sequence complementary to the nucleobase sequence of miR-234.

Provided herein are methods for the prevention of fibrosis. Such methods comprise administering to a subject having or at risk of developing fibrosis a compound comprising a modified oligonucleotide consisting of 8 to 25 linked nucleosides, and having a nucleobase sequence complementary to the nucleobase sequence of miR-214, and thereby preventing or delaying the onset of the fibrosis.

In certain embodiments, the fibrosis is kidney fibrosis. In certain embodiments, the kidney fibrosis results from one or more of a disease selected from tubulointerstitial fibrosis, IgA nephropathy, interstitial fibrosis/tubular atrophy; chronic kidney damage, glomerular disease, glomerulonephritis, diabetes mellitus, idiopathy focal segmental glomerulosclerosis, membranous nephropathy, collapsing glomerulopathy, chronic recurrent kidney infection, and end stage renal disease. In certain embodiments, the kidney fibrosis results from acute kidney injury, chronic kidney injury, surgery, chemotherapy, radiation treatment, allograft rejection, chronic transplant rejection, and acute transplant rejection.

In certain embodiments, the fibrosis is liver fibrosis. In certain embodiments, the liver fibrosis is present in a subject having a disease selected from chronic liver injury, hepatitis infection, non-alchoholic steatohepatitis, and cirrhosis. In certain embodiments, the fibrosis is pulmonary fibrosis. In certain embodiments, the pulmonary fibrosis is idiopathic pulmonary fibrosis. In certain embodiments, a subject having pulmonary fibrosis has chronic obstructive pulmonary disease. In certain embodiments, the fibrosis is restenosis-related vascular fibrosis. In certain embodiments, the fibrosis is spleen fibrosis. In certain embodiments, the fibrosis is age-related fibrosis. In certain embodiments, the fibrosis is skin fibrosis. In certain embodiments, the subject has scleroderma.

In certain embodiments, the methods provided herein comprise improving one or more symptoms of fibrosis. In certain embodiments, the methods provided herein comprise reducing fibrosis. In certain embodiments, the methods provided herein comprise preventing progression of fibrosis. In certain embodiments, the methods provided herein comprise delaying the progression of fibrosis. In certain embodiments, the methods provided herein comprise reducing fibrosis.

Also provided herein are methods for treating post-transplantation fibrosis comprising administering to a transplant subject a compound comprising a modified oligonucleotide consisting of 8 to 25 linked nucleosides, and having a nucleobase sequence complementary to the nucleobase sequence of miR-214, thereby treating post-transplantation fibrosis.

Further provided herein are methods for preventing post-transplantation fibrosis comprising administering to a transplant subject a compound comprising a modified oligonucleotide consisting of 8 to 25 linked nucleosides, and having a nucleobase sequence complementary to the nucleobase sequence of miR-214, thereby preventing post-transplantation fibrosis.

Also provided herein are methods for delaying the onset of post-transplantation fibrosis comprising administering to a transplant subject a compound comprising a modified oligonucleotide consisting of 8 to 25 linked nucleosides, and having a nucleobase sequence complementary to the nucleobase sequence of miR-214, thereby delaying the onset of post-transplantation fibrosis. In certain, embodiments, the transplantation-associated fibrosis is post-transplantation kidney fibrosis. In certain embodiments, the post-transplantation fibrosis is transplantation-associated liver fibrosis. In certain embodiments, the compound is administered prior to transplantation. In certain embodiments, the compound is administered following transplantation. In certain embodiments, the compound is administered before and after transplantation.

In certain embodiments, any of the methods provided herein may comprise administering at least one additional therapy. In certain embodiments, the at least one additional therapy comprises a therapeutic agent. In certain embodiments, the at least one additional therapeutic agent is selected from an anti-inflammatory agent, an anti-diabetic agent, and an anti-connective tissue growth factor therapy. In certain embodiments, the at least one additional therapy comprises surgery.

In certain embodiments, the administration comprises parenteral administration. In certain embodiments, the administration comprises pulmonary administration. In certain embodiments, the pulmonary administration comprises administration through an inhaler.

Provided herein are subjects for improving organ function in a subject having fibrosis. In certain embodiments, the administering improves organ function in the subject, wherein the organ function is selected from cardiac function, pulmonary function, liver function, and kidney function.

In certain, embodiments, provided herein are methods for assessing kidney function in a subject comprising measuring blood urea nitrogen in the blood of the subject; measuring creatinine in the blood of the subject; measuring creatinine clearance in the subject; measuring proteinuria in the subject; measuring albumin:Cr ratio in the subject; and/or measuring urinary output in the subject.

In certain embodiments, provided herein are methods for assessing liver function in a subject comprising measuring alanine aminotransferase levels in the blood of the subject; measuring aspartate aminotransferase levels in the blood of the subject; measuring bilirubin levels in the blood of the subject; measuring albumin levels in the blood of the subject; measuring prothrombin time in the subject; measuring ascites in the subject; and/or measuring encephalopathy in the subject.

In certain embodiments, provided herein are methods for assessing lung function in a subject comprising measuring vital capacity in the subject; measuring forced vital capacity in the subject; measuring forced expiratory volume in one second in the subject; measuring peak expiratory flow rate in the subject; measuring forced expiratory flow in the subject; measuring maximal voluntary ventilation in the subject; determining the ratio of forced expiratory volume in one second to forced vital capacity in the subject; measuring ventilation/perfusion ratio in the subject; measuring nitrogen washout in the subject; and/or measuring absolute volume of air in one or more lungs of a subject.

In certain embodiments provided herein are methods for assessing cardiac function comprising measuring cardiac output in the subject; measuring stroke volume in the subject; measuring mean systolic ejection rate in the subject; measuring systolic blood pressure in the subject; measuring left ventricular ejection fraction in the subject; determining stroke index in the subject; determining cardiac index in the subject; measuring left ventricular percent fractional shortening in the subject; measuring mean velocity of circumferential fiber shortening in the subject; measuring left ventricular inflow velocity pattern in the subject; measuring pulmonary venous flow velocity pattern in the subject; and/or measuring peak early diastolic velocity of the mitral annulus of the subject.

Provided herein are methods comprising contacting a cell or tissue with a compound comprising a modified oligonucleotide consisting of 8 to 25 linked nucleosides, wherein the nucleobase sequence of the modified oligonucleotide is complementary to the nucleobase sequence of miR-214. In certain embodiments, the cell is an epithelial cell. In certain embodiments, the contacting prevents the epithelial cell from undergoing an epithelial to mesenchymal transition. In certain embodiments, the contacting delays the epithelial cell from undergoing an epithelial to mesenchymal transition. In certain embodiments, the epithelial cell is a kidney epithelial cell. In certain embodiments, the epithelial cell is a liver epithelial cell. In certain embodiments, the epithelial cell is a lung epithelial cell. In certain embodiments, the cell or tissue is a kidney cell or tissue. In certain embodiments, the cell or tissue is in vivo.

Provided herein are methods of preventing metastasis of a cancer cell comprising contacting a cancer cell with a compound comprising a modified oligonucleotide consisting of 8 to 25 linked nucleosides, wherein the nucleobase sequence of the modified oligonucleotide is complementary to the nucleobase sequence of miR-214, thereby preventing metastasis of the cancer cell. In certain embodiments, the cancer cell is in vivo. Provided herein are methods for preventing metastasis comprising administering to a subject having cancer with a compound comprising a modified oligonucleotide consisting of 8 to 25 linked nucleosides, wherein the nucleobase sequence of the modified oligonucleotide is complementary to the nucleobase sequence of miR-214, thereby preventing metastasis the cancer. In certain embodiments, the cancer is selected from liver cancer, breast cancer, lung cancer, colon cancer, ovarian cancer, cervical cancer, brain cancer, esophageal cancer, kidney cancer, melanoma, oral cancer, pancreatic cancer, prostate cancer, rectal cancer, stomach cancer, bladder cancer, thyroid cancer, and testicular cancer.

In certain embodiments, the subject is a human.

In certain embodiments, the compound consists of the modified oligonucleotide. In certain embodiments, the nucleobase sequence of the modified oligonucleotide is at least 85% complementary to a nucleobase sequence selected from SEQ ID NO: 1 and 2. In certain embodiments, the nucleobase sequence of the modified oligonucleotide is at least 90% complementary to a nucleobase sequence selected from SEQ ID NO: 1 and 2. In certain embodiments, the nucleobase sequence of the modified oligonucleotide is at least 95% complementary to a nucleobase sequence selected from SEQ ID NO: 1 and 2. In certain embodiments, the nucleobase sequence of the modified oligonucleotide is fully complementary to a nucleobase sequence selected from SEQ ID NO: 1 and 2. In certain embodiments, the nucleobase sequence of the modified oligonucleotide has no more than two mismatches to a nucleobase sequence selected from SEQ ID NO: 1 and 2. In certain embodiments, the nucleobase sequence of the modified oligonucleotide has no more than one mismatch to a nucleobase sequence selected from SEQ ID NO: 1 and 2. In certain embodiments, the nucleobase sequence of the modified oligonucleotide has one mismatch to a nucleobase sequence selected from SEQ ID NO: 1 and 2. In certain embodiments, the nucleobase sequence of the modified oligonucleotide has no mismatches to a nucleobase sequence selected from SEQ ID NO: 1 and 2. In certain embodiments, the nucleobase sequence of the modified oligonucleotide comprises a nucleobase sequence selected from SEQ ID NOs: 3, 4, 5, 6, 7, 8, 9, 10, 11, 12, 13, 14, 15, 16, 17, and 18. In certain embodiments, the nucleobase sequence of the modified oligonucleotide consists of a nucleobase sequence selected from SEQ ID NOs: 3, 4, 5, 6, 7, 8, 9, 10, 11, 12, 13, 14, 15, 16, and 17.

Provided herein are compositions comprising a compound comprising a modified oligonucleotide consisting of 8 to 25 linked nucleosides, wherein the nucleobase sequence of the modified oligonucleotide is complementary to the nucleobase sequence of miR-214.

In certain embodiments, the modified oligonucleotide consists of 8 linked nucleosides. In certain embodiments, the modified oligonucleotide consists of 9 linked nucleosides. In certain embodiments, the modified oligonucleotide consists of 10 linked nucleosides. In certain embodiments, the modified oligonucleotide consists of 11 linked nucleosides. In certain embodiments, the modified oligonucleotide consists of 12 linked nucleosides. In certain embodiments, the modified oligonucleotide consists of 13 linked nucleosides. In certain embodiments, the modified oligonucleotide consists of 14 linked nucleosides. In certain embodiments, the modified oligonucleotide consists of 15 linked nucleosides. In certain embodiments, the modified oligonucleotide consists of 16 linked nucleosides. In certain embodiments, the modified oligonucleotide consists of 17 linked nucleosides. In certain embodiments, the modified oligonucleotide consists of 18 linked nucleosides. In certain embodiments, the modified oligonucleotide consists of 19 linked nucleosides. In certain embodiments, the modified oligonucleotide consists of 20 linked nucleosides. In certain embodiments, the modified oligonucleotide consists of 21 linked nucleosides. In certain embodiments, the modified oligonucleotide consists of 22 linked nucleosides. In certain embodiments, the modified oligonucleotide consists of 23 linked nucleosides. In certain embodiments, the modified oligonucleotide consists of 24 linked nucleosides.

In certain embodiments, the modified oligonucleotide comprises at least one modified internucleoside linkage. In certain embodiments, the modified oligonucleotide comprises at least two modified internucleoside linkages. In certain embodiments, the modified oligonucleotide comprises at least three modified internucleoside linkages. In certain embodiments, the first and last internucleoside linkages of the modified oligonucleotide are modified internucleoside linkages. In certain embodiments, each internucleoside linkage of the modified oligonucleotide is a modified internucleoside linkage. In certain embodiments, at least one modified internucleoside linkage is a phosphorothioate internucleoside linkage.

In certain embodiments, the modified oligonucleotide comprises at least one nucleoside comprising a modified sugar. In certain embodiments, the modified oligonucleotide comprises at least two nucleosides comprising a modified sugar. In certain embodiments, the modified oligonucleotide comprises at least three nucleosides comprising a modified sugar. In certain embodiments, each nucleoside of the modified oligonucleotide comprises a modified sugar. In certain embodiments, each nucleoside of the modified oligonucleotide comprises a 2'-O-methoxyethyl sugar. In certain embodiments, the modified oligonucleotide comprises a plurality of nucleosides comprising a 2'-O-methoxyethyl sugar and a plurality of nucleosides comprising a 2'-fluoro sugar modification. In certain embodiments, each modified sugar is independently selected from a 2'-O-methoxyethyl sugar, a 2'-fluoro sugar, 2'-O-methyl sugar, and a bicyclic sugar moiety. In certain embodiments, the bicyclic sugar moiety an LNA sugar moiety. In certain embodiments, the bicyclic sugar moiety a cEt sugar moiety. In certain embodiments, the cEt sugar moiety is a S-cEt sugar moiety. In certain embodiments, the cEt sugar moiety is an R-cEt sugar moiety.

In certain embodiments, the modified oligonucleotide comprises at least one β-D-deoxyribonucleoside.

In certain embodiments, the compound consists of the modified oligonucleotide; the modified oligonucleotide has the entire nucleobase sequence of SEQ ID NO: 3; each internucleoside linkage of the modified oligonucleotide is a phosphorothioate internucleoside linkage; nucleosides 1, 2, 12, 13, 14, 21, and 22 are 2'-O-methoxyethyl nucleosides; nucleosides 3, 4, 5, 6, 7, 8, 9, 10, 11, 15, 16, 17, 18, 19, and 20 are 2'-fluoro nucleosides; and nucleoside 2 comprises a 5-methylcytosine.

BRIEF DESCRIPTION OF THE FIGURE

FIG. 1 shows a meta-analysis of the effect of anti-miR-214 on (A) collagen content and (B) hydroxyproline content in the kidneys of mice that underwent UUO surgery, as described in Example 2. Each data point represents a separate study with 7 to 8 animals per group.

DETAILED DESCRIPTION

Unless defined otherwise, all technical and scientific terms used herein have the same meaning as is commonly understood by one of skill in the arts to which the invention belongs. Unless specific definitions are provided, the nomenclature utilized in connection with, and the procedures and techniques of, analytical chemistry, synthetic organic chemistry, and medicinal and pharmaceutical chemistry described herein are those well known and commonly used in the art. In the event that there is a plurality of definitions for terms herein, those in this section prevail. Standard techniques may be used for chemical synthesis, chemical analysis, pharmaceutical preparation, formulation and delivery, and treatment of subjects. Certain such techniques and procedures may be found for example in "Carbohydrate Modifications in Antisense Research" Edited by Sangvi and Cook, American Chemical Society, Washington D.C., 1994; and "Remington's Pharmaceutical Sciences," Mack Publishing Co., Easton, Pa., 18th edition, 1990; and which is hereby incorporated by reference for any purpose. Where permitted, all patents, patent applications, published applications and publications, GENBANK sequences, websites and other published materials referred to throughout the entire disclosure herein, unless noted otherwise, are incorporated by reference in their entirety. Where reference is made to a URL or other such identifier or address, it is understood that such identifiers can change and particular information on the internet can command go, but equivalent information can be found by searching the internet. Reference thereto evidences the availability and public dissemination of such information.

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

DEFINITIONS

"Fibrosis" means the formation or development of excess fibrous connective tissue in an organ or tissue. In certain embodiments, fibrosis occurs as a reparative or reactive process. In certain embodiments, fibrosis occurs in response to damage or injury. The term "fibrosis" is to be understood as the formation or development of excess fibrous connective tissue in an organ or tissue as a reparative or reactive process, as opposed to a formation of fibrous tissue as a normal constituent of an organ or tissue.

"Subject suspected of having" means a subject exhibiting one or more clinical indicators of a disease.

"Subject suspected of having fibrosis" means a subject exhibiting one or more clinical indicators of fibrosis.

"Fibroblast" means a cell that gives rise to connective tissue.

"Fibroproliferative disorder" means a disorder characterized by excessive proliferation and/or activation of fibroblasts.

"Metastasis" means the process by which cancer spreads from the place at which it first arose as a primary tumor to other locations in the body. The metastatic progression of a primary tumor reflects multiple stages, including dissociation from neighboring primary tumor cells, survival in the circulation, and growth in a secondary location.

"Anti-miR" means an oligonucleotide having nucleobase sequence complementary to a microRNA. In certain embodiments, an anti-miR is a modified oligonucleotide.

"Anti-miR-214" means an oligonucleotide having a nucleobase sequence complementary to miR-214. In certain embodiments, an anti-miR-214 is fully complementary to miR-214. In certain embodiments, an anti-miR-254 is at least 80%, at least 85%, at least 90%, or at least 95% complementary to miR-214. In certain embodiments, an anti-miR-214 is a modified oligonucleotide.

"Subject" means a human or non-human animal selected for treatment or therapy.

"Subject in need thereof" means the state in which a subject is identified as in need of a therapy or treatment.

"Administering" means providing a pharmaceutical agent or composition to a subject, and includes, but is not limited to, administering by a medical professional and self-administering.

"Parenteral administration" means administration through injection or infusion. Parenteral administration includes, but is not limited to, subcutaneous administration, intravenous administration, or intramuscular administration.

"Subcutaneous administration" means administration just below the skin.

"Intravenous administration" means administration into a vein.

"Intracardial administration" means administration into the heart. In certain embodiments, intracardial administration occurs by way of a catheter. In certain embodiments, intracardial administration occurs by way of open heart surgery.

"Pulmonary administration" means administration to the lungs.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Duration" means die period of time during which an activity or event continues. In certain embodiments, the duration of treatment is the period of time during which doses of a pharmaceutical agent or pharmaceutical composition are administered.

"Therapy" means a disease treatment method. In certain embodiments, therapy includes, but is not limited to, chemotherapy, radiation therapy, or administration of a pharmaceutical agent.

"Treatment" means the application of one or more specific procedures used for the cure or amelioration of a disease. In certain embodiments, the specific procedure is the administration of one or more pharmaceutical agents.

"Amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"At risk for developing" means the state in which a subject is predisposed to developing a condition or disease. In certain embodiments, a subject at risk for developing a condition or disease exhibits one or more symptoms of the condition or disease, but does not exhibit a sufficient number of symptoms to be diagnosed with the condition, or disease. In certain embodiments, a subject at risk for developing a condition or disease exhibits one or more symptoms of the condition or disease, but to a lesser extent required to be diagnosed with the condition or disease.

"Prevent the onset of" means to prevent the development a condition or disease in a subject who is at risk for developing the disease or condition. In certain, embodiments, a subject at risk for developing the disease or condition receives treatment similar to the treatment received by a subject who already has the disease or condition.

"Delay the onset of" means to delay the development of a condition or disease in a subject who is at risk for developing the disease or condition. In certain embodiments, a subject at risk for developing the disease or condition receives treatment similar to the treatment received by a subject who already has the disease or condition.

"Therapeutic agent" means a pharmaceutical agent used for the cure, amelioration or prevention of a disease.

"Dose" means a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

"Dosage unit" means a form in which a pharmaceutical agent is provided. In certain embodiments, a dosage unit is a vial containing lyophilized oligonucleotide. In certain embodiments, a dosage unit is a vial containing reconstituted oligonucleotide.

"Therapeutically effective amount" refers to an amount of a pharmaceutical agent that provides a therapeutic benefit to an animal.

"Pharmaceutical composition" means a mixture of substances suitable for administering to an individual that includes a pharmaceutical agent. For example, a pharmaceutical composition may comprise a sterile aqueous solution.

"Pharmaceutical agent" means a substance that provides a therapeutic effect when administered to a subject.

"Active pharmaceutical ingredient" means the substance in a pharmaceutical composition that provides a desired effect.

"Improved liver function" means the change in liver function toward normal limits. In certain embodiments, liver function is assessed by measuring molecules found in a subject's blood. For example, in certain embodiments, improved liver function is measured by a reduction in blood liver transaminase levels.

"Acceptable safety profile" means a pattern of side effects that is within clinically acceptable limits.

"Side effect" means a physiological response attributable to a treatment other than desired effects. In certain embodiments, side effects include, without limitation, injection site reactions, liver function test abnormalities, renal function abnormalities, liver toxicity, renal toxicity, central nervous system abnormalities, and myopathies. Such side effects may be detected directly or indirectly. For example, increased aminotransferase levels in serum may indicate liver toxicity or liver function abnormality. For example, increased bilirubin may indicate liver toxicity or liver function abnormality.

"Injection site reaction" means inflammation or abnormal redness of skin at a site of injection in an individual.

"Subject compliance" means adherence to a recommended or prescribed therapy by a subject.

"Comply" means the adherence with a recommended therapy by a subject.

"Recommended therapy" means a treatment recommended by a medical professional for the treatment, amelioration, or prevention of a disease.

"Target nucleic acid" means a nucleic acid to which an oligomeric compound is designed to hybridize.

"Targeting" means the process of design and selection of nucleobase sequence that will hybridize to a target nucleic acid.

"Targeted to" means having a nucleobase sequence that will allow hybridization to a target nucleic acid.

"Target engagement" means the interaction of a drug with its target molecule in a manner that changes the activity, expression or level of the target. In certain embodiments, target engagement means an anti-miR interacting with its microRNA target, such that the activity of the microRNA is inhibited.

"Modulation" means to a perturbation of function or activity. In certain embodiments, modulation means an increase in activity. In certain embodiments, modulation means a decrease in activity.

"Expression" means any functions and steps by which a gene's coded information is converted into structures present and operating in a cell.

"5' target site" refers to the nucleobase of a target nucleic acid which is complementary to the 5'-most nucleobase of a particular oligonucleotide.

"3' target site" means the nucleobase of a target nucleic acid which is complementary to the 3'-most nucleobase of a particular oligonucleotide.

"Region" means a portion of linked nucleosides within a nucleic acid. In certain embodiments, an oligonucleotide has a nucleobase sequence that is complementary to a region of a target nucleic acid. For example, in certain such embodiments an oligonucleotide is complementary to a region of a miRNA stem-loop sequence. In certain such embodiments, an oligonucleotide is fully complementary to a region of a miRNA stem-loop sequence.

"Segment" means a smaller or sub-portion of a region.

"Nucleobase sequence" means the order of contiguous nucleobases, in a 5' to 3' orientation, independent of any sugar, linkage, and/or nucleobase modification.

"Contiguous nucleobases" means nucleobases immediately adjacent to each other in a nucleic acid.

"Nucleobase complementarity" means the ability of two nucleobases to pair non-covalently via hydrogen bonding.

"Complementary" means that an oligomeric compound is capable of hybrizing to a target nucleic acid under stringent hybridization conditions.

"Fully complementary" means each nucleobase of an oligomeric compound is capable of pairing with a nucleobase at each corresponding position in a target nucleic acid. For example, in certain embodiments, an oligomeric compound wherein each nucleobase has complementarity to a nucleobase within a region of a miRNA stem-loop sequence is fully complementary to the miRNA stem-loop sequence.

"Percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound. In certain embodiments, percent complementarity means the number of nucleobases that are complementary to the target nucleic acid, divided by the total number of nucleobases of the modified oligonucleotide.

"Percent identity" means the number of nucleobases in first nucleic acid that are identical to nucleobases at corresponding positions in a second nucleic acid, divided by the total number of nucleobases in the first nucleic acid.

"Hybridize" means the annealing of complementary nucleic acids that occurs through nucleobase complementarity.

"Mismatch" means a nucleobase of a first nucleic acid that is not capable of pairing with a nucleobase at a corresponding position of a second nucleic acid.

"Identical" means having the same nucleobase sequence.

"miR-214" means the mature miRNA having the nucleobase sequence set forth in SEQ ID NO: 1 (ACAGCAGGCACAGACAGGCAGU).

"miR-214 stem-loop sequence" means the miR-214 precursor having the nucleobase sequence set forth in SEQ ID NO: 2 (GGCCUGGCUGGACAGAGUUGUCAUGUGUCUGCCUGUCUACACUUGCUGUGCAGAACAUCCGCUCACCUGUACAGCAGGCACAGACAGGCAGUCACAUGACAACCCAGCCU).

"MicroRNA" means an endogenous non-coding RNA between 18 and 25 nucleobases in length, which is the product of cleavage of a pre-miRNA by the enzyme Dicer. Examples of mature miRNAs are found in the miRNA database known as miRBase (http://microrna.sanger.ac.uk/). In certain embodiments, microRNA is abbreviated as "miRNA" or "miR."

"Pre-miRNA" or "pre-miR" means a non-coding RNA having a hairpin structure, which is the product of cleavage of a pri-miR by the double-stranded RNA-specific ribonuclease known as Drosha.

"Stem-loop sequence" means an RNA having a hairpin structure and containing a mature miRNA sequence. Pre-miRNA sequences and stem-loop sequences may overlap. Examples of stem-loop sequences are found in the miRNA database known as miRBase (http://microrna.sanger.ac.uk/).

"Pri-miRNA" or "pri-miR" means a non-coding RNA having a hairpin structure that is a substrate for the double-stranded RNA-specific ribonuclease Drosha.

"miRNA precursor" means a transcript that originates from a genomic DNA and that comprises a non-coding, structured RNA comprising one or more miRNA sequences. For example, in certain embodiments a miRNA precursor is a pre-miRNA. In certain embodiments, a miRNA precursor is a pri-miRNA.

"Monocistronic transcript" means a miRNA precursor containing a single miRNA sequence.

"Polycistronic transcript" means a miRNA precursor containing two or more miRNA sequences.

"Seed sequence" means a nucleobase sequence comprising from 6 to 8 contiguous nucleobases of nucleobases 1 to 8 of the 5'-end of a mature microRNA sequence.

"Seed match sequence" means a nucleobase sequence that is complementary to a seed sequence, and is the same length as the seed sequence.

"Oligomeric compound" means a compound comprising a polymer of linked monomeric subunits.

"Oligonucleotide" means a polymer of linked nucleosides, each of which can be modified or unmodified, independent from one another.

"Naturally occurring internucleoside linkage" means a 3' to 5' phosphodiester linkage between nucleosides.

"Natural sugar" means a sugar found in DNA (2'-H) or RNA (2'-OH).

"Natural nucleobase" means a nucleobase that is unmodified relative to its naturally occurring form.

"Internucleoside linkage" means a covalent linkage between adjacent nucleosides.

"Linked nucleosides" means nucleosides joined by a covalent linkage.

"Nucleobase" means a heterocyclic moiety capable of non-covalently pairing with another nucleobase.

"Nucleoside" means a nucleobase linked to a sugar.

"Nucleotide" means a nucleoside having a phosphate group covalently linked to the sugar portion of a nucleoside.

"Compound comprising an oligonucleotide consisting of" a number of linked nucleosides means a compound that includes an oligonucleotide having the specified number of linked nucleosides. Thus, the compound may include additional substituents or conjugates. Unless otherwise indicated, the compound does not include any additional nucleosides beyond those of the oligonucleotide.

"Compound comprising a modified oligonucleotide consisting of" a number of linked nucleosides means a compound that includes a modified oligonucleotide having the specified number of linked nucleosides. Thus, the compound may include additional substituents or conjugates. Unless otherwise indicated, the compound does not include any additional nucleosides beyond those of the modified oligonucleotide.

"Modified oligonucleotide" means an oligonucleotide having one or more modifications relative to a naturally occurring terminus, sugar, nucleobase, and/or internucleoside linkage.

"Single-stranded modified oligonucleotide" means a modified oligonucleotide which is not hybridized to a complementary strand.

"Modified internucleoside linkage" means any change from a naturally occurring internucleoside linkage.

"Phosphorothioate internucleoside linkage" means a linkage between nucleosides where one of the non-bridging atoms is a sulfur atom.

"Modified sugar" means substitution and/or any change from a natural sugar.

"Modified nucleobase" means any substitution and/or change from a natural nucleobase.

"5-methylcytosine" means a cytosine modified with a methyl group attached to the 5' position.

"2'-O-methyl sugar" or "2'-OMe sugar" means a sugar having a O-methyl modification at the 2' position.

"2'-O-methoxyethyl sugar" or "2'-MOE sugar" means a sugar having a O-methoxyethyl modification at the 2' position.

"2'-O-fluoro" or "2'-F" means a sugar having a fluoro modification of the 2' position.

"Bicyclic sugar moiety" means a sugar modified by the bridging of two non-geminal ring atoms.

"Locked nucleic acid (LNA) sugar moiety" means a substituted sugar moiety having a ($CH_2$)—O bridge between the 4' and 2' furanose ring atoms.

"ENA sugar moiety" means a substituted sugar moiety having a ($CH_2$)$_2$—O bridge between the 4' and 2' furanose ring atoms.

"Constrained ethyl (cEt) sugar moiety" means a substituted sugar moiety having a $CH(CH_3)$—O bridge between the 4' and the 2' furanose ring atoms. In certain embodiments, the $CH(CH_3)$—O bridge is constrained in the S orientation. In certain embodiments, the ($CH_2$)$_2$—O is constrained in the R orientation.

"S-cEt sugar moiety" means a substituted sugar moiety comprising an S-constrained $CH(CH_3)$—O bridge between the 4' and the 2' furanose ring atoms.

"R-cEt sugar moiety" means a substituted sugar moiety comprising an R-constrained $CH(CH_3)$—O bridge between the 4' and the 2' furanose ring atoms.

"2'-O-methoxyethyl nucleoside" means a 2'-modified nucleoside having a 2'-O-methoxyethyl sugar modification.

"2'-fluoro nucleoside" means a 2'-modified nucleoside having a 2'-fluoro sugar modification.

"2'-O-methyl" nucleoside means a 2'-modified nucleoside having a 2'-O-methyl sugar modification.

"Bicyclic nucleoside" means a 2'-modified nucleoside having a bicyclic sugar moiety.

"cEt nucleoside" means a nucleoside comprising a cEt sugar moiety. A cEt nucleoside may comprise a modified or unmodified nucleobase.

"S-cEt nucleoside" means a nucleoside comprising an S-cEt sugar moiety.

"R-cEt nucleoside" means a nucleoside comprising an R-cEt sugar moiety.

"Non-bicyclic nucleoside" means a nucleoside that has a sugar other than a bicyclic sugar. In certain embodiments, a non-bicyclic nucleoside comprises a naturally occurring sugar. In certain embodiments, a non-bicyclic nucleoside comprises a modified sugar. In certain embodiments, a non-bicyclic nucleoside is a β-D-deoxyribonucleoside. In certain embodiments, a non-bicyclic nucleoside is a 2'-O-methoxyethyl nucleoside.

"β-D-deoxyribonucleoside" means a naturally occurring DNA nucleoside. A β-D-deoxyribonucleoside may comprise a modified or unmodified nucleobase.

"β-D-ribonucleoside" means a naturally occurring RNA nucleoside. A β-D-ribonucleoside may comprise a modified or unmodified nucleobase.

"LNA nucleoside" means a nucleoside comprising a LNA sugar moiety.

"ENA nucleoside" means a nucleoside comprising an ENA sugar moiety.

"Motif" means a pattern of modified and/or unmodified nucleobases, sugars, and/or internucleoside linkages in an oligonucleotide.

A "fully modified oligonucleotide" means each nucleobase, each sugar, and/or each internucleoside linkage is modified.

A "uniformly modified oligonucleotide" means each nucleobase, each sugar, and/or each internucleoside linkage has the same modification throughout the modified oligonucleotide.

A "gapmer" means a modified oligonucleotide having an internal region of linked nucleosides positioned between two external regions of linked nucleosides, where the nucleosides of the internal region comprise a sugar moiety different than that of the nucleosides of each external region.

A "gap segment" is an internal region of a gapmer that is positioned between the external regions.

A "wing segment" is an external region of a gapmer that is located at the 5' or 3' terminus of the internal region.

A "symmetric gapmer" means each nucleoside of each external region comprises the same sugar modification.

An "asymmetric gapmer" means each nucleoside of one external region comprises a first sugar modification, and each nucleoside of the other external region comprises a second sugar modification.

A "stabilizing modification" means a modification to a nucleoside that provides enhanced stability to a modified oligonucleotide, in the presence of nucleases, relative to that provided by 2'-deoxynucleosides linked by phosphodiester internucleoside linkages. For example, in certain embodiments, a stabilizing modification is a stabilizing nucleoside modification. In certain embodiments, a stabilizing modification is a internucleoside linkage modification.

A "stabilizing nucleoside" means a nucleoside modified to provide enhanced nuclease stability to an oligonucleotide, relative to that provided by a 2'-deoxynucleoside. In one embodiment, a stabilizing nucleoside is a 2'-modified nucleoside.

A "stabilizing internucleoside linkage" means an internucleoside linkage that provides improved nuclease stability to an oligonucleotide relative to that provided by a phosphodiester internucleoside linkage. In one embodiment, a stabilizing internucleoside linkage is a phosphorothioate internucleoside linkage.

Overview

A normal physiological response to damage or injury in an organ or tissue involves repair by connective tissue. However, under some conditions, this repair process occurs in excess, resulting in fibrosis. The formation of this excess fibrous connective tissue contributes to abnormal changes in tissue architecture and interferes with normal organ function.

Fibrosis can occur in any part of the body, and can result from a variety of physical, metabolic, ischemic, infectious, inflammatory or immunological injuries. Although the anatomical locations, origins, and clinical manifestations of fibrosis may be diverse, there are important pathological features common to all types of fibrosis. Regardless of the location in which fibrosis occurs, the fibrotic process involves the secretion and activation of profibrotic cytokines, the expansion and activation of mesenchymal cell populations, and extracellular matrix synthesis and organization, and ultimately leads to the destruction of normal tissue. Left untreated, fibrosis can lead to a variety of conditions of the heart, lungs, kidney, liver, and skin, among other tissues.

Fibroblasts are the most common cells found in connective tissue, and are responsible for the synthesis of reticulin and other elastic fibres which support the extracellular matrix and play an important part in wound healing (Sempowski, G. D. et al., 2002. Wound Repair Regeneration. 3: 120-131). As such, inappropriate fibroblast activity contributes to fibrosis. Fibroblasts are thought to originate from epithelial-mesenchymal transition (EMT) (Iwano, M. et al., 2002. J. Clin. Invest. 110: 341-50). Epithelial-mesenchymal transition (EMT) describes a series of rapid changes of cell phenotype (Kalluri, R. and Neilson, E. G. 2003. J. Clin. Invest. 112: 1776-1784) during which static epithelial cells lose cell-cell contacts, acquire mesenchymal features and manifest a migratory phenotype.

EMT occurs in normal physiological processes, including as part of the normal healing process, but has also been linked to disease states. For example, EMT has been implicated in forming fibroblasts in injured tissues, including progressive kidney diseases, pulmonary fibrosis, and possibly liver fibrosis (Strutz, F. et al., J. Cell. Biol. 30: 393-405; Iwano, M. et al., 2002. J. Clin. Invest. 110: 341-50; Chilosi, M. et al., 2003. Am. J. Pathol. 162: 1495-502; Ikegami, T. et al., 2007. Cells Tissues Organs. 185: 213-221). Additionally, EMT has been connected to the process of metastasis. The relevance of EMT in tumor progression has been explored in several studies (Greenburg, G. and Hay, E. 1986. Dev. Biol. 115: 363-379; Boyer, B. et al., 1989. J. Cell. Biol. 109: 1495-1509; Uehara, Y. et al., 1992. J. Cell. Biol. 117: 889-894). Epithelial cells are held together through integrins to an underlying extracellular matrix (ECM) called the basement membrane. Mesenchymal cells, on the other hand, have the ability to invade and move through the three-dimensional structure of the ECM. Therefore, EMT at least superficially resembles the transformation of normal adherent cells into the metastatic phenotype.

It is demonstrated herein that the expression of microRNA miR-214 is elevated in fibrotic tissue samples. It is further demonstrated herein that fibrosis is reduced following inhibition of miR-214 in experimental models of fibrosis. Further, it has been found that miR-214 expression correlates with extracellular matrix and collagen gene ontology pathways using multiple tumor microarray datasets (data not shown). Accordingly, provided herein are compositions and methods for the treatment, prevention and/or delaying the onset of fibrosis. The fibrosis may be fibrosis of any tissue or organ, including but not limited to liver, kidney, heart, skin, and lung.

Conditions and Treatments

Provided herein are compositions and methods for treating, preventing, or delaying the onset of fibrosis, comprising administering a compound comprising a modified oligonucleotide, wherein the modified oligonucleotide is complementary to miR-214, to a subject. The subject may have received a diagnosis of fibrosis, may be at risk for developing fibrosis, or may be suspected of having fibrosis.

In certain embodiments, a subject having fibrosis has kidney fibrosis. In certain embodiments, the kidney fibrosis is glomerulosclerosis. In certain embodiments, the kidney fibrosis is tubulointerstitial fibrosis.

Fibrosis of the kidney may result from any disease that leads to chrome kidney damage. In certain embodiments, a subject having kidney fibrosis has IgA nephropathy. In certain embodiments, a subject having kidney fibrosis has interstitial fibrosis/tubular atrophy. In certain embodiments, a subject having kidney fibrosis has a glomerular disease. In certain embodiments, a subject having kidney fibrosis has glomerulonephritis. In certain embodiments, a subject having kidney fibrosis has diabetes mellitus. In certain embodiments, a subject having kidney fibrosis has idiopathic focal segmental glomerulosclerosis. In certain embodiments a subject having kidney fibrosis has membranous nephropathy. In certain embodiments a subject having fibrosis has collapsing glomerulopathy. In certain embodiments a subject having kidney fibrosis has chronic recurrent kidney infection. In certain embodiments a subject having kidney fibrosis has end stage renal disease.

In certain embodiments, a subject having kidney fibrosis has hypertension. In certain embodiments, the hypertension is systemic hypertension. In certain embodiments, the hypertension is intraglomerular hypertension.

In certain embodiments, a subject having fibrosis has a kidney disease or condition. In certain embodiments, a subject at risk for developing fibrosis has a kidney disease or condition. In certain embodiments, a subject suspected of having fibrosis has a kidney disease or condition. Accordingly, provided herein are methods for treating a subject having, at risk for developing, or suspected of having fibrosis, wherein the subject has a kidney disease or condition. The kidney disease or condition may be one or more of, without limitation, glomerularnephritis, diabetes mellitus, idiopathic focal segmental glomerulosclerosis, membranous nephropathy, collapsing glomerulopathy, chronic recurrent kidney infection, or end stage renal disease.

In certain embodiments, a subject having fibrosis has kidney fibrosis that results from acute or repetitive trauma to the kidney. In certain embodiments, trauma results from surgery, chemotherapy, radiation treatment, allograft rejection, chronic transplant rejection, and acute transplant rejection.

In certain embodiments, a subject having fibrosis has a liver disease or condition. In certain embodiments, a subject at risk for developing fibrosis has a liver disease or condition. In certain embodiments, a subject suspected of having fibrosis has a liver disease or condition. Accordingly, provided herein are methods for treating a subject having, at risk for developing, or suspected of having fibrosis, wherein the subject has a liver disease or condition. In certain embodiments, a liver disease or condition is chronic liver injury. In certain embodiments, a liver disease or condition is hepatitis virus infection. In certain embodiments, a hepatitis infection is hepatitis C virus infection. In certain embodiments a liver disease or condition is non-alcoholic steatohepatitis, non-alcoholic fatty liver disease, alcoholic steatohepatitis, or alcoholic liver disease. In certain embodiments a liver disease or condition is cirrhosis. In certain embodiments a subject has bridging fibrosis.

In certain embodiments, a subject having fibrosis has at least one other disease or condition which is a lung disease or condition. In certain embodiments, a subject at risk for developing fibrosis has at least one other disease or condition which is a lung disease or condition. In certain embodiments, a subject suspected of having fibrosis has at least one other disease or condition which is a lung disease or condition. Accordingly, provided herein are methods for the treatment of a subject having, at risk for developing, or suspected of having fibrosis, wherein the subject has at least one lung disease or condition. In certain embodiments a lung disease or condition is chronic obstructive lung disease.

In certain embodiments the fibrosis is cardiac fibrosis.

In certain embodiments the fibrosis is skin fibrosis. In certain embodiments the fibrosis is age-related fibrosis. In certain embodiments the fibrosis is spleen fibrosis.

Scleroderma is a chronic autoimmune disease characterized by fibrosis, among other symptoms. In certain embodiments, a subject having fibrosis has scleroderma.

Fibrosis frequently occurs in transplanted organs, leading to loss of organ function and ultimately to chronic rejection of the transplanted organ. Prevention or treatment of fibrosis in transplanted organs may prevent or delay chronic rejection of the transplanted organ, or in other words may prolong function of the transplanted organ. Accordingly, in certain embodiments a subject has post-transplant fibrosis. In certain embodiments, the post-transplant fibrosis is kidney post-transplant fibrosis. In certain embodiments, the transplantation associated fibrosis is liver post-transplant fibrosis. In certain embodiments, a compound described herein is administered prior to transplantation. In certain embodiments, a compound described herein is administered concurrently with transplantation. In certain embodiments, a compound described herein is administered following transplantation.

Provided herein are methods for treating a subject having a fibroproliferative disorder. In certain embodiments such methods comprise administering to a subject having or suspected of having a fibroproliferative disorder a modified oligonucleotide having a nucleobase sequence which is complementary to a miRNA or a precursor thereof. In certain embodiments, the miRNA is miR-214.

Provided herein are methods for treating, preventing or delaying the onset of metastasis. In certain embodiments, the subject has cancer. In certain embodiments, the cancer is liver cancer, breast cancer, lung cancer, colon cancer, ovarian cancer, cervical cancer, leukemia, lymphoma, brain cancer, esophageal cancer, Hodgkin lymphoma, non-Hodgkin lymphoma, kidney cancer, melanoma, myeloma, oral cancer, pancreatic cancer, prostate cancer, rectal cancer, stomach cancer, bladder cancer, thyroid cancer, or testitcular cancer.

Provided herein are methods for treating, preventing or delaying the onset of a fibroproliferative disorder.

Certain Phenotypes

Provided herein are compositions and methods for reducing or preventing fibroblast proliferation or activation.

Provided herein are methods for modulating the epithelial-mesenchymal transition (EMT). Such methods comprise contacting an epithelial cell with a compound consisting of a modified oligonucleotide, wherein the modified oligonucleotide is complementary to miR-214. In certain embodiments, the contacting delays the transition of an epithelial cell to a fibroblast. In certain embodiments, the contacting prevents the transition of an epithelial cell to a fibroblast.

In certain embodiments, the epithelial cell is a cancer cell in certain embodiments, the contacting delays the metastasis of the cancer cell. In certain embodiments, the contacting prevents metastasis of the cancer cell.

Certain Clinical Outcomes

In certain embodiments, administration of the compounds or methods provided herein result in one or more clinically desirable outcomes in a subject. Such improvements may be used to determine the extent to which a subject is responding to treatment.

In certain embodiments a clinically desirable outcome is the amelioration of fibrosis. In certain embodiments a clinically desirable outcome is the slowing of further progression of fibrosis. In certain embodiments a clinically desirable outcome is the halting of further progression of fibrosis. In certain embodiments a clinically desirable outcome is a reduction in fibrosis. In certain embodiments a clinically desirable outcome is a reduction in collagen content in the organ having fibrosis.

In certain embodiments a clinically desirable outcome is the amelioration of kidney fibrosis. In certain embodiments a clinically desirable outcome is the slowing of further progression of kidney fibrosis. In certain embodiments a clinically desirable outcome is the halting of further progression of kidney fibrosis. In certain embodiments a clinically desirable outcome is a reduction in kidney fibrosis. In certain embodiments a clinically desirable outcome is a reduction in collagen content in the kidney.

In certain embodiments a clinically desirable outcome is improved kidney function. Kidney function may be assessed by one or more known methods commonly performed in a clinical setting, including, without limitation: measuring blood urea nitrogen in the blood of the subject; measuring creatinine in the blood of the subject; measuring creatinine clearance in the subject; measuring proteinuria in the subject; measuring microalbumin:creatinine ratio in the subject; and/or measuring urinary output in the subject.

In certain embodiments, a clinically desirable outcome is improved liver function. Liver function may be assessed by one or more known methods commonly performed in a clinical setting, including, without limitation: measuring alanine aminotransferase levels in the blood of the subject; measuring aspartate aminotransferase levels in the blood of the subject; measuring bilirubin levels in the blood of the subject; measuring albumin levels in the blood of the subject; measuring prothrombin time in the subject; measuring ascites in the subject; and/or measuring encephalopathy in the subject.

In certain embodiments a clinically desirable outcome is improved lung function in a subject having pulmonary fibrosis. In certain embodiments the subject has idiopathic pulmonary fibrosis. Lung function may be assessed by one or more known methods commonly performed in a clinical setting, including, without limitation: measuring vital capacity in the subject; measuring forced vital capacity in the subject; measuring forced expiratory volume in one second in the subject; measuring peak expiratory flow rate in the subject; measuring forced expiratory flow in the subject; measuring maximal voluntary ventilation in the subject; determining the ratio of forced expiratory volume in one second to forced vital capacity in the subject; measuring ventilation/perfusion ratio in the subject; measuring nitrogen washout in the subject; and/or measuring absolute volume of air in one or more lungs of a subject.

In certain embodiments a clinically desirable outcome is improved cardiac function in a subject having cardiac fibrosis. Cardiac function may be assessed by one or more known methods commonly performed in a clinical setting, including, without limitation: measuring cardiac output in the subject; measuring stroke volume in the subject; measuring mean systolic ejection rate in the subject; measuring systolic blood pressure in the subject; measuring left ventricular ejection fraction in the subject; determining stroke index in the subject; determining cardiac index in the subject; measuring left ventricular percent fractional shortening in the subject; measuring mean velocity of circumferential fiber shortening in the subject; measuring left ventricular inflow velocity pattern in the subject; and measuring pulmonary venous flow velocity pattern in the subject; and/or measuring peak early diastolic velocity of the mitral annulus of the subject.

Certain Additional Therapies

Treatments for fibrosis may comprise more than one therapy. As such, in certain embodiments provided herein are methods for treating a subject having or suspected of having fibrosis comprising administering at least one therapy in addition to administering a modified oligonucleotide having a nucleobase sequence complementary to a miR-214.

In certain embodiments, the at least one additional therapy comprises a pharmaceutical agent.

In certain embodiments, pharmaceutical agents include anti-inflammatory agents. In certain embodiments, an anti-inflammatory agent is a steroidal anti-inflammatory agent. In certain embodiments, a steroid anti-inflammatory agent is a corticosteroid. In certain embodiments, a corticosteroid, is prednisone. In certain embodiments, an anti-inflammatory agent is a non-steroidal anti-inflammatory drugs. In certain embodiments, a non-steroidal anti-inflammatory agent is ibuprofen, a COX-1 inhibitor, or a COX-2 inhibitor.

In certain embodiments, pharmaceutical agents include immunosuppressive agents. In certain embodiments, an immunosuppressive agent is a corticosteroid, cyclophosphamide, or mycophenolate mofetil.

In certain embodiments, pharmaceutical agents include angiotensin II receptor blockers (ARB). In certain embodiments, an angiotensin II receptor blocker is candesartan, irbesartan, ohmesartan, losartan, valsartan, telmisartan, or eprosartan.

In certain embodiments, pharmaceutical agents include anti-diabetic agent. Antidiabetic agents include, but are not limited to, biguanides, glucosidase inhibitors, insulins, sulfonylureas, and thiazolidenediones.

In certain embodiments, pharmaceutical agents include angiotensin II receptor blockers (ARB). In certain embodiments, an angiotensin II receptor blocker is candesartan, irbesartan, olmesartan, losartan, valsartan, telmisartan, or eprosartan.

In certain embodiments, pharmaceutical agents include, but are not limited to, diuretics (e.g. spironolactone, eplerenone, furosemide), inotropes (e.g. dobutamine, milrinone), digoxin, vasodilators, angiotensin II converting enzyme (ACE) inhibitors (e.g. are captopril, enalapril, lisinopril, benazepril, quinapril, fosinopril, and ramipril), calcium channel blockers, isosorbide dinitrate, hydralazine, nitrates (e.g. isosorbide mononitrate, isosorbide dinitrate), hydralazine, beta-blockers (e.g. carvedilol, metoprolol), and natriuretic peptides (e.g. nesiritide).

In certain embodiments, pharmaceutical agents include heparinoids. In certain embodiments, a heparinoid is pentosan polysulfate.

In certain embodiments, a pharmaceutical agent is a pharmaceutical agent that blocks one or more responses to fibrogenic signals.

In certain embodiments, a pharmaceutical agent is an anti-connective tissue growth factor therapy. In certain embodiments, an anti-CTGF therapy is a monoclonal antibody against CTGF.

In certain embodiments, an additional therapy may be a pharmaceutical agent that enhances the body's immune system, including low-dose cyclophosphamide, thymostimulin, vitamins and nutritional supplements (e.g., antioxidants, including vitamins A, C, E, beta-carotene, zinc, selenium, glutathione, coenzyme Q-10 and echinacea), and vaccines, e.g., the immunostimulating complex (ISCOM), which comprises a vaccine formulation that combines a multimeric presentation of antigen and an adjuvant.

In certain embodiments, the additional therapy is selected to treat or ameliorate a side effect of one or more pharmaceutical compositions of the present invention. Such side effects include, without limitation, injection site reactions, liver function test abnormalities, renal function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality.

Further examples of additional pharmaceutical agents include, but are not limited to, immunoglobulins, including, but not limited to intravenous immunoglobulin (IVIg); analgesics (e.g., acetaminophen); salicylates; antibiotics; antivirals; antifungal agents; adrenergic modifiers; hormones (e.g., anabolic steroids, androgen, estrogen, calcitonin, progestin, somatostan, and thyroid hormones); immunomodulators; muscle relaxants; antihistamines; osteoporosis agents (e.g., biphosphonates, calcitonin, and estrogens); prostaglandins, antineoplastic agents; psychotherapeutic agents; sedatives; poison oak or poison sumac products; antibodies; and vaccines.

Cancer treatments often comprise more man one therapy. As such, in certain embodiments the present invention provides methods for reducing or preventing metastasis comprising administering to a subject a compound comprising a modified oligonucleotide, wherein the modified oligonucleotide is complementary to miR-214, and administering at least one additional therapy that is an anti-cancer therapy.

In certain embodiments, an anti-cancer therapy is chemotherapy. Suitable chemotherapeutic agents include docetaxel, cyclophosphamide, ifosfamide, methotrexate, vinblastine, cisplatin, 5-fluorouracil, gemcitabine, doxorubicine, mitomycin c, sorafenib, etoposide, carboplatin, epirubicin, irinotecan and oxaliplatin. An additional suitable chemotherapeutic agent includes an oligomeric compound, other than a composition of the present invention, that is used to treat cancer.

In certain embodiments, an anti-cancer therapy is radiation therapy. In certain embodiments, an anti-cancer therapy is surgical resection of a tumor.

Certain Routes of Administration

In certain embodiments, administering to a subject comprises parenteral administration. In certain embodiments, administering to a subject comprises intravenous administration. In certain embodiments, administering to a subject comprises subcutaneous administration.

In certain embodiments, administering to a subject comprises intraarterial administration. In certain embodiments, administering to a subject comprises intracardial administration. Suitable means for intracardial administration include the use of a catheter, or administration during open heart surgery. In certain, embodiments, administration comprises use of a stent.

In certain embodiments, administration includes pulmonary administration. In certain embodiments, pulmonary administration comprises delivery of aerosolized oligonucleotide to the lung of a subject by inhalation. Following inhalation by a subject of aerosolized oligonucleotide, oligonucleotide distributes to cells of both normal and inflamed lung tissue, including alveolar macrophages, eosinophils, epithelium, blood vessel endothelium, and bronchiolar epithelium. A suitable device for the delivery of a pharmaceutical composition comprising a modified oligonucleotide includes, but is not limited to, a standard nebulizer device. Formulations and methods for modulating the size of droplets using nebulizer devices to target specific portions of the respiratory tract and lungs are well known to those skilled in the art. Additional suitable devices include dry powder inhalers or metered dose inhalers.

In certain embodiments, pharmaceutical compositions are administered to achieve local rather than systemic exposures. For example, pulmonary administration delivers a pharmaceutical composition to the lung, with minimal systemic exposure.

Additional suitable administration routes include, but are not limited to, oral, rectal, transmucosal, intestinal, enteral, topical, suppository, intrathecal, intraventricular, intraperitoneal intranasal, intraocular, intramuscular, intramedullary, and intratumoral.

Certain Compounds

The compounds provided herein are useful for the treatment, amelioration and/or prevention of cardiac diseases. In certain embodiments, the compound comprises an oligonucleotide. In certain such embodiments, the compound consists of an oligonucleotide. In certain embodiments, the oligonucleotide is a modified oligonucleotide. In certain embodiments, a modified oligonucleotide is complementary to miR-214.

In certain such embodiments, the compound comprises an oligonucleotide hybridized to a complementary strand, i.e. the compound comprises a double-stranded oligomeric compound. In certain embodiments, the hybridization of an oligonucleotide to a complementary strand forms at least one blunt end. In certain such embodiments, the hybridization of an oligonucleotide to a complementary strand forms a blunt end at each terminus of the double-stranded oligomeric compound. In certain embodiments, a terminus of an oligonucleotide comprises one or more additional linked nucleosides relative to the number of linked nucleosides of the complementary strand. In certain embodiments, the one or more additional nucleosides are at the 5' terminus of an oligonucleotide. In certain embodiments, the one or more additional nucleosides are at the 3' terminus of an oligonucleotide. In certain embodiments, at least one nucleobase of a nucleoside of the one or more additional nucleosides is complementary to the target RNA. In certain embodiments, each nucleobase of each one or more additional nucleosides is complementary to the target RNA. In certain embodiments, a terminus of the complementary strand comprises one or more additional linked nucleosides relative to the number of linked nucleosides of an oligonucleotide. In certain embodiments, the one or more additional linked nucleosides are at the 3' terminus of the complementary strand. In certain embodiments, the one or more additional linked nucleosides are at the 5' terminus of the complementary strand. In certain embodiments, two additional linked nucleosides are linked to a terminus. In certain embodiments, one additional nucleoside is linked to a terminus.

In certain embodiments, the compound comprises an oligonucleotide conjugated to one or more moieties which enhance the activity, cellular distribution or cellular uptake of the resulting antisense oligonucleotides. In certain such embodiments, the moiety is a cholesterol moiety. In certain embodiments, the moiety is a lipid moiety. Additional moieties for conjugation include carbohydrates, phospholipids, biotin, phenazine, folate, phenanthridine, anthraquinone, acridine, fluoresceins, rhodamines, coumarins, and dyes. In certain embodiments, a conjugate group is attached directly to an oligonucleotide. In certain embodiments, a conjugate group is attached to an oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl)cyclohexane-1-carboxylate (SMCC), 6-aminohexanoic acid (AHEX or AHA), substituted C1-C10 alkyl substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl nitro, thiol, thioalkoxy, halogen, alkyl, aryl, alkenyl and alkynyl.

In certain such embodiments, the compound comprises an oligonucleotide having one or more stabilizing groups that are attached to one or both termini of an oligonucleotide to enhance properties such as, for example, nuclease stability. Included in stabilizing groups are cap structures. These terminal modifications protect an oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-aminoalkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5-amino, a bridging and/or non-bridging 5'-phosphoramidate, a phosphorothioate, and a 5'-mercapto moiety.

Certain Nucleobase Sequences

In certain embodiments, an oligonucleotide has a nucleobase sequence that is complementary to the nucleobase sequence of a miR-214 or a precursor thereof. Nucleobase sequences of mature miRNAs and their corresponding stem-loop sequences described herein are the sequences found in miRBase, an online searchable database of miRNA sequences and annotation, found at http://microrna.sanger.ac.uk/. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 14.0 of the miRBase sequence database and sequences described in any earlier Release of the miRBase sequence database. A sequence database release may result in the re-naming of certain miRNAs. The compositions of the present invention encompass modified oligonucleotides that are complementary to any nucleobase sequence version of the miRNAs described herein.

In certain embodiments, an oligonucleotide has a nucleobase sequence that is complementary to miR-214 or a precursor thereof. Accordingly, in certain embodiments the nucleobase sequence of an oligonucleotide may have one or more mismatched basepairs with respect to its target miRNA or precursor sequence, and remains capable of hybridizing to its target sequence. In certain embodiments, an oligonucleotide has a nucleobase sequence that is fully complementary to miR-214 or a precursor thereof.

In certain embodiments, an oligonucleotide has a sequence that is complementary to the nucleobase sequence of the miR-214 stem-loop: 5'-UGUCGGGUAGCU UAUCA-GACUGAUGUUGACUGUUGAAUCUCAUG-GCAACACCAGUCGAUGGGCUGUCUG ACA-3' (SEQ ID NO:2)

In certain embodiments, an oligonucleotide has a sequence that is complementary to a nucleobase sequence of miR-214, where the nucleobase sequence of miR-214 is ACAGCAG-GCACAGACAGGCAGU (SEQ ID NO; 1).

In certain embodiments, an oligonucleotide has a nucleobase sequence that is complementary to a region of the miR-214 stem-loop sequence (SEQ ID NO: 2). In certain embodiments, an oligonucleotide has a nucleobase sequence that is complementary to the region of nucleobases 8-29 of SEQ ID NO: 2.

In certain embodiments, an oligonucleotide has a nucleobase sequence that is complementary to the nucleobase sequence of miR-214 (SEQ ID NO: 1). In certain embodiments, an oligonucleotide has a nucleobase sequence comprising the nucleobase sequence ACTGCCTGTCTGTGC-CTGCTGT (SEQ ID NO: 3). In certain embodiments, an oligonucleotide has a nucleobase sequence consisting of the nucleobase sequence ACTGCCTGTCTGTGCCTGCTGT (SEQ ID NO: 3). In certain embodiments, an oligonucleotide has a nucleobase sequence comprising a nucleobase sequence selected from the table below. In certain embodiments an oligonucleotide has a nucleobase sequence consisting of a nucleobase sequence selected from the table below.

| Nucleobase sequence (5' to 3') | Length (in nucleobases) | SEQ ID NO: |
|---|---|---|
| ACTGCCTGTCTGTGCCTGCTGT | 22 | 3 |
| CTGCCTGTCTGTGCCTGCTGT | 21 | 4 |
| TGCCTGTCTGTGCCTGCTGT | 20 | 5 |
| GCCTGTCTGTGCCTGCTGT | 19 | 6 |
| CCTGTCTGTGCCTGCTGT | 18 | 7 |
| CTGTCTGTGCCTGCTGT | 17 | 8 |
| TGTCTGTGCCTGCTGT | 16 | 9 |
| GTCTGTGCCTGCTGT | 15 | 10 |
| TCTGTGCCTGCTGT | 14 | 11 |
| CTGTGCCTGCTGT | 13 | 12 |
| TGTGCCTGCTGT | 12 | 13 |
| GTGCCTGCTGT | 11 | 14 |
| TGCCTGCTGT | 10 | 15 |
| GCCTGCTGT | 9 | 16 |
| CCTGCTGT | 8 | 17 |
| CTGCTGT | 7 | 18 |

In certain embodiments, an oligonucleotide comprises a nucleobase sequence that is complementary to a seed sequence of miR-214. In certain embodiments, an oligonucleotide consists of a nucleobase sequence that is complementary to a seed sequence of miR-214. Modified oligonucleotides complementary to the seed sequence of a miRNA have been shown to inhibit activity of the miRNA. Such inhibitory activity is described in PCT Publication No. WO 2009/043353, which is herein incorporated by reference in its entirety for its description of modified oligonucleotides targeting miRNA seed sequences.

In certain embodiments, a seed sequence is a hexamer seed sequence. In certain such embodiments, a seed sequence is nucleobases 1-6 of SEQ ID NO: 1 (ACAGCA; SEQ ID NO: 19). In certain such embodiments, a seed sequence is nucleobases 2-7 of SEQ ID NO: 1 (CAGCAG; SEQ ID NO: 20). In certain such embodiments, a seed sequence is nucleobases 3-8 of SEQ ID NO: 1 (AGCAGG; SEQ ID NO: 21).

In certain embodiments, a seed sequence is a heptamer seed sequence. In certain such embodiments, a heptamer seed sequence is nucleobases 1-7 of SEQ ID NO: 1 (ACAGCAG; SEQ ID NO: 22). In certain such embodiments, a heptamer seed sequence is nucleobases 2-8 of SEQ ID NO: 1 (CAG-CAGG; SEQ ID NO: 23).

In certain embodiments, the seed sequence is an octamer seed sequence. In certain such embodiments, an octamer seed sequence is nucleobases 1-8 of SEQ ID NO: 1 (ACAGCAGG; SEQ ID NO: 24). In certain embodiments, an octamer seed sequence is nucleobases 2-9 of SEQ ID NO: 1 (CAGCAGGC; SEQ ID NO: 25). In certain embodiments, a modified oligonucleotide comprises a nucleobase sequence that is complementary to a seed sequence, i.e. a modified oligonucleotide comprises a seed-match sequence. In certain such embodiments, a modified oligonucleotide comprises the nucleobase sequence of SEQ ID NO: 26. In certain such embodiments, a modified oligonucleotide comprises the nucleobase sequence of SEQ ID NO: 27. In certain such embodiments, a modified oligonucleotide comprises the nucleobase sequence of SEQ ID NO; 28. In certain such embodiments, a modified oligonucleotide comprises the nucleobase sequence of SEQ ID NO: 29. In certain such embodiments, a modified oligonucleotide comprises the nucleobase sequence of SEQ ID NO: 17. In certain such embodiments, a modified oligonucleotide comprises the nucleobase sequence of SEQ ID NO: 18. In certain such embodiments, a modified oligonucleotide comprises the nucleobase sequence of SEQ ID NO; 30.

In certain embodiments a modified oligonucleotide consists of 8 linked nucleosides and has the sequence of SEQ ID NO: 30. In certain such embodiments, each nucleoside comprises a modified sugar moiety.

In certain embodiments, a modified oligonucleotide consists of 8 linked nucleosides and has the sequence of SEQ ID NO: 17. In certain such embodiments, each nucleoside comprises a modified sugar moiety.

Certain seed sequences and certain seed-match sequences are set forth in the table below.

| Seed Sequence Type | Seed Sequence (5' to 3') | SEQ ID NO: | Seed Match Sequence (5' to 3') | SEQ ID NO: |
|---|---|---|---|---|
| Hexamer 1-6 | ACAGCA | 19 | TGCTGT | 26 |
| Hexamer 2-7 | CAGCAG | 20 | CTGCTG | 27 |
| Hexamer 3-8 | AGCAGG | 21 | CCTGCT | 28 |
| Heptamer 1-7 | ACAGCAG | 22 | CTGCTGT | 18 |
| Heptamer 2-8 | CAGCAGG | 23 | CCTGCTG | 29 |
| Octamer 1-8 | ACAGCAGG | 24 | CCTGCTGT | 17 |
| Octamer 2-9 | CAGCAGGC | 25 | GCCTGCTG | 30 |

In certain embodiments, a modified oligonucleotide consists of 6 linked nucleosides. In certain embodiments, a modified oligonucleotide consists of 7 linked nucleosides. In certain embodiments, the modified oligonucleotide consists of 8 linked nucleosides. In certain embodiments, a modified oligonucleotide consists of 9 linked nucleosides. In certain embodiments, a modified oligonucleotide consists of 10 linked nucleosides. In certain embodiments, a modified oligonucleotide consists of 11 linked nucleosides. In certain embodiments, a modified oligonucleotide consists of 12 linked nucleosides.

In certain embodiments, an oligonucleotide has a nucleobase sequence that is complementary to a nucleobase sequence having at least 80% identity to a nucleobase sequence of a miR-214 stem-loop sequence (SEQ ID NO: 2). In certain embodiments, an oligonucleotide has a nucleobase sequence that is complementary to a nucleobase sequence having at least 85%, at least 90%, at least 92%, at least 94%, at least 96%, at least 98% identity, or 100% identity to a nucleobase sequence of a miR-214 stem-loop sequence (SEQ ID NO: 2).

In certain embodiments, an oligonucleotide has a nucleobase sequence that is complementary to a nucleobase sequence having at least 80% identity to the nucleobase sequence of SEQ ID NO: 1. In certain embodiments, an oligonucleotide has a nucleobase sequence that is complementary to a nucleobase sequence having at least 85%, at least 90%, at least 92%, at least 94%, at least 96%, at least 98% identity, or 100% identity to the nucleobase sequence of SEQ ID NO: 1.

In certain embodiments, a nucleobase sequence of an oligonucleotide is fully complementary to a miRNA nucleobase sequence listed herein, or a precursor thereof. In certain embodiments, an oligonucleotide has a nucleobase sequence having one mismatch with respect to the nucleobase sequence of the mature miRNA, or a precursor thereof. In certain embodiments, an oligonucleotide has a nucleobase sequence having two mismatches with respect to the nucleobase sequence of the miRNA, or a precursor thereof. In certain such embodiments, an oligonucleotide has a nucleobase sequence having no more than two mismatches with respect to the nucleobase sequence of the mature miRNA, or a precursor thereof. In certain such embodiments, the mismatched nucleobases are contiguous. In certain such embodiments, the mismatched nucleobases are not contiguous.

In certain embodiments, an oligonucleotide consists of a number of linked nucleosides that is equal to the length of the mature miR to which it is complementary.

In certain embodiments, the number of linked nucleosides of an oligonucleotide is less than the length of the mature miRNA to which it is complementary. In certain such embodiments, the number of linked nucleosides of an oligonucleotide is one less than the length of the mature miR to which it is complementary. In certain such embodiments, an oligonucleotide has one less nucleoside at the 5' terminus. In certain such embodiments, an oligonucleotide has one less nucleoside at the 3' terminus. In certain such embodiments, an oligonucleotide has two fewer nucleosides at the 5' terminus. In certain such embodiments, an oligonucleotide has two fewer nucleosides at the 3' terminus. An oligonucleotide having a number of linked nucleosides that is less than the length of the miRNA, wherein each nucleobase of an oligonucleotide is complementary to each nucleobase at a corresponding position in a miRNA, is considered to be an oligonucleotide having a nucleobase sequence that is fully complementary to a portion of a miRNA sequence.

In certain embodiments, the number of linked nucleosides of an oligonucleotide is greater than the length of the miRNA to which it is complementary. In certain such embodiments, the nucleobase of an additional nucleoside is complementary to a nucleobase of a miRNA stem-loop sequence. In certain embodiments, the number of linked nucleosides of an oligonucleotide is one greater than the length of the miRNA to which it is complementary. In certain such embodiments, the additional nucleoside is at the 5' terminus of an oligonucleotide. In certain such embodiments, the additional nucleoside is at the 3' terminus of an oligonucleotide. In certain embodiments, the number of linked nucleosides of an oligonucleotide is two greater than the length of the miRNA to which it is complementary. In certain such embodiments, the two additional nucleosides are at the 5' terminus of an oligonucleotide. In certain such embodiments, the two additional nucleosides are at the 3' terminus of an oligonucleotide. In certain such embodiments, one additional nucleoside is located at the 5' terminus and one additional nucleoside is located at the 3' terminus of an oligonucleotide.

In certain embodiments, a portion of the nucleobase sequence of an oligonucleotide is fully complementary to the nucleobase sequence of the miRNA, but the entire modified oligonucleotide is not fully complementary to the miRNA. In certain such embodiments, the number of nucleosides of an oligonucleotide having a fully complementary portion is greater than the length of the miRNA. For example, an oligonucleotide consisting of 24 linked nucleosides, where the nucleobases of nucleosides 1 through 23 are each complementary to a corresponding position of a miRNA that is 23 nucleobases in length, has a 23 nucleoside portion that is fully complementary to the nucleobase sequence of the miRNA and approximately 96% overall complementarity to the nucleobase sequence of the miRNA.

In certain embodiments, the nucleobase sequence of an oligonucleotide is fully complementary to a portion of the nucleobase sequence of a miRNA. For example, an oligonucleotide consisting of 22 linked nucleosides, where the nucleobases of nucleosides 1 through 22 are each complementary to a corresponding position of a miRNA that is 23 nucleobases in length, is fully complementary to a 22 nucleobase portion of the nucleobase sequence of a miRNA. Such an oligonucleotide has approximately 96% overall complementarity to the nucleobase sequence of the entire miRNA, and has 100% complementarity to a 22 nucleobase portion of the miRNA.

In certain embodiments, a portion of the nucleobase sequence of an oligonucleotide is fully complementary to a portion of the nucleobase sequence of a miRNA, or a precursor thereof. In certain such embodiments, 15 contiguous nucleobases of an oligonucleotide are each complementary to 15 contiguous nucleobases of a miRNA, or a precursor thereof. In certain such embodiments, 16 contiguous nucleobases of an oligonucleotide are each complementary to 16 contiguous nucleobases of a miRNA, or a precursor thereof. In certain such embodiments, 17 contiguous nucleobases of an oligonucleotide are each complementary to 17 contiguous nucleobases of a miRNA, or a precursor thereof. In certain such embodiments, 18 contiguous nucleobases of an oligonucleotide are each complementary to 18 contiguous nucleobases of a miRNA, or a precursor thereof. In certain such embodiments, 19 contiguous nucleobases of an oligonucleotide are each complementary to 19 contiguous nucleobases of a miRNA, or a precursor thereof. In certain such embodiments, 20 contiguous nucleobases of an oligonucleotide are each complementary to 20 contiguous nucleobases of a miRNA, or a precursor thereof. In certain such embodiments, 22 contiguous nucleobases of an oligonucleotide are each complementary to 22 contiguous nucleobases of a miRNA, or a precursor thereof. In certain such embodiments, 23 contiguous nucleobases of an oligonucleotide are each complementary to 23 contiguous nucleobases of a miRNA, or a precursor thereof. In certain such embodiments, 24 contiguous nucleobases of an oligonucleotide are each complementary to 24 contiguous nucleobases of a miRNA, or a precursor thereof.

The nucleobase sequences set forth herein, including but not limited, to those found in the Examples and in the sequence listing, are independent of any modification to the nucleic acid. As such, nucleic adds defined by a SEQ ID NO may comprise, independently, one or more modifications to one or more sugar moieties, to one or more internucleoside linkages, and/or to one or more nucleobases.

Although the sequence listing accompanying this filing identifies each nucleobase sequence as either "RNA" or "DNA" as required, in practice, those sequences may be modified with any combination of chemical modifications. One of skill in the art will readily appreciate that such designation as "RNA" or "DNA" to describe modified oligonucleotides is somewhat arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine(methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such, as those having sequence "AUCGAUCG" and those having some DNA bases and some RNA bases such as "AUCGATCG" and oligomeric compounds having other modified bases, such as "ATmeC-GAUCG," wherein meC indicates a cytosine base comprising a methyl group at the 5-position.

Certain Oligonucleotides

In certain embodiments, an oligonucleotide consists of 8 to 25 linked nucleosides. In certain embodiments, an oligonucleotide consists of 15 to 23 linked nucleosides. In certain embodiments, an oligonucleotide consists of 15 to 30 linked nucleosides. In certain embodiments, an oligonucleotide consists of 19 to 24 linked nucleosides. In certain embodiments, an oligonucleotide consists of 21 to 24 linked nucleosides.

In certain embodiments, an oligonucleotide consists of 8 linked nucleosides. In certain embodiments, an oligonucleotide consists of 9 linked nucleosides. In certain embodiments, an oligonucleotide consists of 10 linked nucleosides. In certain embodiments, an oligonucleotide consists of 11 linked nucleosides. In certain embodiments, an oligonucleotide consists of 12 linked nucleosides. In certain embodiments, an oligonucleotide consists of 13 linked nucleosides. In certain embodiments, an oligonucleotide consists of 14 linked nucleosides. In certain embodiments, an oligonucleotide consists of 15 linked nucleosides. In certain embodiments, an oligonucleotide consists of 16 linked nucleosides. In certain embodiments, an oligonucleotide consists of 17 linked nucleosides. In certain embodiments, an oligonucleotide consists of 18 linked nucleosides. In certain embodiments, an oligonucleotide consists of 19 linked nucleosides. In certain embodiments, an oligonucleotide consists of 20 linked nucleosides. In certain embodiments, an oligonucleotide consists of 21 linked nucleosides. In certain embodiments, an oligonucleotide consists of 22 linked nucleosides. In certain embodiments, an oligonucleotide consists of 23 linked, nucleosides. In certain embodiments, an oligonucleotide consists of 24 linked nucleosides. In certain embodiments, an oligonucleotide consists of 25 linked nucleosides. In certain embodiments, an oligonucleotide consists of 26 linked nucleosides. In certain embodiments, an oligonucleotide consists of 27 linked nucleosides. In certain embodiments, an oligonucleotide consists of 28 linked nucleosides. In certain embodiments, an oligonucleotide consists of 29 linked nucleosides. In certain embodiments, an oligonucleotide consists of 30 linked nucleosides.

Certain Modifications

In certain embodiments, oligonucleotides provided herein may comprise one or more modifications to a nucleobase, sugar, and/or internucleoside linkage, and as such is a modified oligonucleotide. A modified nucleobase, sugar, and/or internucleoside linkage may be selected over an unmodified form because of desirable properties such as, for example, enhanced cellular uptake, enhanced affinity for other oligonucleotides or nucleic acid targets and increased stability in the presence of nucleases.

In certain embodiments, a modified oligonucleotide comprises one or more modified nucleosides. In certain such embodiments, a modified nucleoside is a stabilizing nucleoside. An example of a stabilizing nucleoside is a sugar-modified nucleoside.

In certain embodiments, a modified nucleoside is a sugar-modified nucleoside. In certain such embodiments, the sugar-modified nucleosides can further comprise a natural or modified heterocyclic base moiety and/or a natural or modified internucleoside linkage and may include further modifications independent from the sugar modification. In certain embodiments, a sugar modified nucleoside is a 2'-modified nucleoside, wherein the sugar ring is modified at the 2' carbon from natural ribose or 2'-deoxy-ribose.

In certain embodiments, a 2-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In certain such embodiments, the bicyclic sugar moiety is an L sugar in the beta configuration.

In certain embodiments, the bicyclic sugar moiety comprises a bridge group between the 2' and the 4'-carbon atoms. In certain such embodiments, the bridge group comprises from 1 to 8 linked biradical groups. In certain embodiments, the bicyclic sugar moiety comprises from 1 to 4 linked biradical groups. In certain embodiments, the bicyclic sugar moiety comprises 2 or 3 linked biradical groups. In certain embodiments, the bicyclic sugar moiety comprises 2 linked biradical groups. In certain embodiments, a linked biradical group is selected from —O—, —S—, —N($R_1$)—, —C($R_1$)($R_2$)—, —C($R_1$)=C($R_1$)—, —C($R_1$)=N—, —C(=N$R_1$)—, —Si($R_1$)($R_2$)—, —S(=O)$_2$—, —S(=O)—, —C(=O)— and —C(=S)—; where each $R_1$ and $R_2$ is, independently, H, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical heteroaryl, substituted heteroaryl, $C_5$-$C_7$ alicyclic radical, substituted $C_5$-$C_7$ alicyclic radical, halogen, substituted oxy (—O—), amino, substituted amino, azido, carboxyl, substituted carboxyl, acyl, substituted acyl, CN, thiol, substituted thiol, sulfonyl (S(=O)$_2$—H), substituted sulfonyl, sulfoxyl (S(=O)—H) or substituted sulfoxyl; and each substituted group is, independently, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, amino, substituted amino, acyl, substituted acyl, $C_1$-$C_{12}$ aminoalkyl, $C_1$-$C_{12}$ aminoalkoxy, substituted $C_1$-$C_{12}$ aminoalkyl substituted $C_1$-$C_{12}$ aminoalkoxy or a protecting group.

In some embodiments, the bicyclic sugar moiety is bridged between the 2' and 4' carbon atoms with a biradical group selected from —O—(CH$_2$)$_p$—, —O—CH$_2$—, —O—CH$_2$CH$_2$—, —O—CH(alkyl)-, —NH—(CH$_2$)$_p$—, —N(alkyl)-(CH$_2$)$_p$—, —O—CH(alkyl)-, —(CH(alkyl))-(CH$_2$)$_p$—, —NH—O—(CH$_2$)$_p$—, —N(alkyl)-O—(CH$_2$)$_p$—, or —O—N(alkyl)-(CH$_2$)$_p$—, wherein p is 1, 2, 3, 4 or 5 and each alkyl group can be further substituted. In certain embodiments, p is 1, 2 or 3.

In certain embodiments, the bicyclic sugar moiety has a CH(CH$_3$)—O bridge between the 4' and the 2' furanose ring atoms (i.e. the bicyclic sugar moiety is a cEt sugar moiety).

In certain embodiments, a 2'-modified nucleoside comprises a 2'-substituent group selected from halo, allyl, amino, azido, SB, CN, OCN, CF$_3$, OCF$_3$, O-, S-, or N(R$_m$)-alkyl; O-, S-, or N(R$_m$)-alkenyl; O-, S- or N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_a$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl phenyl, nitro (NO$_2$), thiol, thioalkoxy (S-alkyl), halogen, alkyl, aryl, alkenyl and alkynyl.

In certain embodiments, a 2'-modified nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_a$), —O(CH$_2$)$_2$O(CH$_2$)$_2$N(CH$_3$)$_2$, and N-substituted acetamide (O—CH$_2$—C(=O)—N(R$_m$)(R$_n$) where each R$_m$, and R$_n$ is, independently, H, an amino protecting group or substituted or unsubstituted C$_1$-C$_{10}$ alkyl.

In certain embodiments, a 2'-modified nucleoside comprises a 2'-substituent group selected from F, OCF$_3$, O—CH$_3$, OCH$_2$CH$_2$OCH$_3$, 2'-O(CH$_2$)$_2$SCH$_3$, O—(CH$_2$)$_2$—O—N(CH$_3$)$_2$, —O(CH$_2$)$_2$O(CH$_2$N(CH$_3$)$_2$, and O—CH$_2$—C(=O)—N(H)CH$_3$.

In certain embodiments, a 2'-modified nucleoside comprises a 2'-substituent group selected from F, O—CH$_3$, and OCH$_2$CH$_2$OCH$_3$.

In certain embodiments, a sugar-modified nucleoside is a 4'-thio modified nucleoside. In certain embodiments, a sugar-modified nucleoside is a 4'-thio-2'-modified nucleoside. A 4'-thio modified nucleoside has a β-D-ribonucleoside where the 4'-O replaced with 4'-S. A 4'-thio-2'-modified nucleoside is a 4'-thio modified nucleoside having the 2'-OH replaced with a 2'-substituent group. Suitable 2'-substituent groups include 2'-OCH$_3$, 2'-O—(CH$_2$)$_2$—OCH$_3$, and 2'-F.

In certain embodiments, a modified oligonucleotide comprises one or more internucleoside modifications. In certain such embodiments, each internucleoside linkage of an oligonucleotide is a modified internucleoside linkage. In certain embodiments, a modified internucleoside linkage comprises a phosphorus atom.

In certain embodiments, a modified oligonucleotide comprises at least one phosphorothioate internucleoside linkage. In certain embodiments, each internucleoside linkage of a modified oligonucleotide is a phosphorothioate internucleoside linkage.

In certain embodiments, a modified internucleoside linkage does not comprise a phosphorus atom. In certain such embodiments, an internucleoside linkage is formed by a short chain alkyl internucleoside linkage. In certain such embodiments, an internucleoside linkage is formed by a cycloalkyl internucleoside linkages. In certain such embodiments, an internucleoside linkage is formed by a mixed heteroatom and alkyl internucleoside linkage. In certain such embodiments, an internucleoside linkage is formed by a mixed heteroatom and cycloalkyl internucleoside linkages. In certain such embodiments, an internucleoside linkage is formed by one or more short chain heteroatomic internucleoside linkages. In certain such embodiments, an internucleoside linkage is formed by one or more heterocyclic internucleoside linkages. In certain such embodiments, an internucleoside linkage has an amide backbone. In certain such embodiments, an internucleoside linkage has mixed N, O, S and CH$_2$ component parts.

In certain embodiments, a modified oligonucleotide comprises one or more modified nucleobases. In certain embodiments, a modified oligonucleotide comprises one or more 5-methylcytosines. In certain embodiments, each cytosine of a modified oligonucleotide comprises a 5-methylcytosine.

In certain embodiments, a modified nucleobase is selected from 5-hydroxymethyl cytosine, 7-deazaguanine and 7-deazaadenine. In certain embodiments, a modified nucleobase is selected from 7-deaza-adenine, 7-deazaguanosine, 2-aminopyridine and 2-pyridone. In certain embodiments, a modified nucleobase is selected from 5-substituted pyrimidines, 6-azapyrimidines and N-2, N-6 and O-6 substituted purines, including 2 aminopropyladenine, 5-propynyluracil and 5-propynylcytosine.

In certain embodiments, a modified nucleobase comprises a polycyclic heterocycle. In certain embodiments, a modified nucleobase comprises a tricyclic heterocycle. In certain embodiments, a modified nucleobase comprises a phenoxazine derivative. In certain embodiments, the phenoxazine can be further modified to form a nucleobase known in the art as a G-clamp.

Certain Oligonucleotide Motifs

Suitable motifs for modified oligonucleotides of the present invention include, but are not limited to, fully modified, uniformly modified, positionally modified, and gapmer. Modified oligonucleotides having a fully modified motif, including a uniformly modified motif, may be designed to target mature miRNAs. Alternatively, modified oligonucleotides having a fully modified motif, including a uniformly modified motif, may be designed to target certain sites of pri-miRNAs or pre-miRNAs, to block the processing of miRNA precursors into mature miRNAs. Modified oligonucleotides having a fully modified motif or uniformly modified motif are effective inhibitors of miRNA activity.

In certain embodiments, a fully modified oligonucleotide comprises a sugar modification at each nucleoside. In certain such embodiments, pluralities of nucleosides are 2'-O-methoxyethyl nucleosides and the remaining nucleosides are 2'-fluoro nucleosides. In certain such embodiments, each of a plurality of nucleosides is a 2'-O-methoxyethyl nucleoside and each of a plurality of nucleosides is a bicyclic nucleoside. In certain such embodiments, a fully modified oligonucleotide further comprises at least one modified internucleoside linkage. In certain embodiments, each internucleoside linkage of a fully sugar-modified oligonucleotide is a modified internucleoside linkage. In certain embodiments, a fully sugar-modified oligonucleotide further comprises at least one phosphorothioate internucleoside linkage. In certain such embodiments, each internucleoside linkage of a fully sugar-modified oligonucleotide is a phosphorothioate internucleoside linkage.

In certain embodiments, a fully modified oligonucleotide is modified at each internucleoside linkage. In certain such embodiments, each internucleoside linkage of a fully modified oligonucleotide is a phosphorothioate internucleoside linkage.

In certain embodiments, a uniformly modified oligonucleotide comprises the same sugar modification at each nucleoside. In certain such embodiments, each nucleoside of a modified oligonucleotide comprises a 2'-O-methoxyethyl sugar modification. In certain embodiments, each nucleoside of a modified oligonucleotide comprises a 2'-O-methyl sugar modification. In certain embodiments, each nucleoside of a modified oligonucleotide comprises a 2'-fluoro sugar modification. In certain such embodiments, a uniformly modified oligonucleotide further comprises at least one modified internucleoside linkage. In certain embodiments, each internucleoside linkage of a uniformly sugar-modified oligonucleotide is a modified internucleoside linkage. In certain embodiments, a uniformly sugar-modified oligonucleotide further comprises at least one phosphorothioate internucleoside linkage. In certain such embodiments, each internucleoside linkage of a uniformly sugar-modified oligonucleotide is a phosphorothioate internucleoside linkage.

In certain embodiments, a uniformly modified oligonucleoside comprises the same internucleoside linkage modifications throughout. In certain such embodiments, each internucleoside linkage of a uniformly modified oligonucleotide is a phosphorothioate internucleoside linkage.

In certain embodiments, a positionally modified oligonucleotide comprises regions of linked nucleosides, where each nucleoside of each region comprises the same sugar moiety, and where each nucleoside of each region comprises a sugar moiety different from that of an adjacent region.

In certain embodiments, a modified oligonucleotide consisting of linked nucleosides is represented by Formula I:

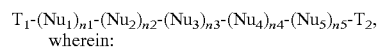

wherein:

$Nu_1$ and $Nu_5$ are, independently, 2' stabilizing nucleosides;
$Nu_2$ and $Nu_4$ are 2'-fluoro nucleosides;
$Nu_3$ is a 2'-modified nucleoside;
each of $n_1$ and $n_5$ is, independently, from 0 to 3;
the sum of $n_2$ plus $n_4$ is between 10 and 25;
$n_3$ is from 0 and 5; and
each $T_1$ and $T_2$ is, independently, H, a hydroxyl protecting group, an optionally linked conjugate group or a capping group.

In certain embodiments, $Nu_1$ and $Nu_5$ are, independently, 2'-modified nucleosides.

In certain embodiments, $Nu_1$ is $O-(CH_2)_2-OCH_3$, $Nu_3$ is $O-(CH_2)_2-OCH_3$, and $Nu_5$ $O-(CH_2)_2-OCH_3$.

In certain embodiments, each internucleoside linkage is a modified internucleoside linkage. In certain such embodiments, each internucleoside is a phosphorothioate linkage.

In certain embodiments, a nucleoside comprises a modified nucleobase. In certain embodiments, where a 2'-O-methoxyethyl nucleoside comprises cytosine, the cytosine is a 5-methylcytosine.

In certain embodiments, $Nu_1$ is $O-(CH_2)_2-OCH_3$, $Nu_3$ is $O-(CH_2)_2-OCH_3$, $Nu_5$ $O-(CH_2)_2-OCH_3$, $T_1$ is H and $T_2$ is H.

In certain embodiments, $T_1$ and $T_2$ are each, independently, H or a hydroxyl protecting group. In certain embodiments, at least one of $T_1$ and $T_2$ is 4,4'-dimethoxytrityl. In certain embodiments, at least one of $T_1$ and $T_2$ is an optionally linked conjugate group. In certain embodiments, at least one of $T_1$ and $T_2$ is a capping group. In certain embodiments, the capping group is an inverted deoxy a basic group.

In certain embodiments, the sum of $n_2$ and $n_4$ is 13. In certain embodiments, the sum of $n_2$ and $n_4$ is 14. In certain embodiments, the sum of $n_2$ and $n_4$ is 15. In certain embodiments, the sum of $n_2$ and $n_4$ is 16. In certain, embodiments, the sum of $n_2$ and $n_4$ is 17. In certain embodiments, the sum of $n_2$ and $n_4$ is 18.

In certain embodiments, $n_1$, $n_2$, and $n_3$ are each, independently, from 1 to 3. In certain embodiments, $n_1$, $n_2$, and $n_3$ are each, independently, from 2 to 3. In certain embodiments, $n_1$ is 1 or 2; $n_2$ is 2 or 3; and $n_3$ is 1 or 2. In certain embodiments, $n_1$ is 2; $n_3$ is 2 or 3; and $n_5$ is 2. In certain embodiments, $n_1$ is 2; $n_3$ is 3; and $n_5$ is 2. In certain embodiments, $n_1$ is 2; $n_3$ is 2; and $n_5$ is 2.

In certain, embodiments, a modified oligonucleotide consists of 20 linked nucleosides. In certain such embodiments, the sum of $n_2$ and $n_4$ is 13; $n_1$ is 2; $n_3$ is 3; and $n_5$ is 2. In certain such embodiments, the sum of $n_2$ and $n_4$ is 14; $n_1$ is 2; $n_3$ is 2; and $n_5$ is 2.

In certain embodiments, a modified oligonucleotide consists of 21 linked nucleosides. In certain such embodiments, the sum of $n_2$ and $n_4$ is 14; $n_1$ is 2; $n_3$ is 3; and $n_5$ is 2. In certain such embodiments, the sum of $n_2$ and $n_4$ is 15; $n_1$ is 2; $n_3$ is 2; and $n_5$ is 2.

In certain embodiments, a modified oligonucleotide consists of 22 linked nucleosides. In certain such embodiments, the sum of $n_2$ and $n_4$ is 15; $n_1$ is 2; $n_3$ is 3; and $n_5$ is 2. In certain such embodiments, the sum of $n_2$ and $n_4$ is 16; $n_1$ is 2; $n_3$ is 2; and $n_5$ is 2.

In certain embodiments, a modified oligonucleotide consists of 23 linked nucleosides. In certain such embodiments, the sum of $n_2$ and $n_4$ is 16; $n_1$ is 2; $n_3$ is 3; and $n_5$ is 2. In certain such embodiments, the sum of $n_2$ and $n_4$ is 17; $n_1$ is 2; $n_3$ is 2; and $n_5$ is 2.

In certain embodiments, a modified oligonucleotide consists of 24 linked nucleosides. In certain such embodiments, the sum of $n_2$ and $n_4$ is 17; $n_1$ is 2; $n_3$ is 3; and $n_5$ is 2. In certain such embodiments, the sum of $n_2$ and $n_4$ is 18; $n_1$ is 2; $n_3$ is 2; and $n_5$ is 2.

In certain embodiments, a modified oligonucleotide consists of 22 linked nucleosides; $n_1$ is 2; $n_2$ is 9; $n_3$ is 3; $n_4$ is 6; $n_5$ is 2; $Nu_1$ is O—$(CH_2)_2$—OCH; $Nu_3$ is O—$(CH_2)_2$—$OCH_3$; and $Nu_5$ O—$(CH_2)_2$—$OCH_3$.

In certain embodiments, a modified oligonucleotide consists of 22 linked nucleosides; $n_1$ is 2; $n_2$ is 9; $n_3$ is 3; $n_4$ is 6; $n_5$ is 2; $Nu_1$ is O—$(CH_2)_2$—$OCH_3$; $Nu_3$ is O—$(CH_2)_2$—$OCH_3$; $Nu_5$ O—$(CH_2)_2$—$OCH_3$; and each internucleoside linkage is a phosphorothioate linkage.

In certain embodiments, a modified oligonucleotide consists of 22 linked nucleosides; $n_1$ is 2; $n_2$ is 9; $n_3$ is 3; $n_4$ is 6; $n_5$ is 2; $Nu_1$ is O—$(CH_2)_2$—$OCH_3$; $Nu_3$ is O—$(CH_2)_2$—$OCH_3$; $Nu_5$ O—$(CH_2)$; internucleoside linkage is a phosphorothioate linkage.

In certain embodiments, a modified oligonucleotide consists of 22 linked nucleosides; has the nucleobase sequence of SEQ ID NO: 3; $n_1$ is 2; $n_2$ is 9; $n_3$ is 3; $n_4$ is 6; $n_5$ is 2; $Nu_1$ is O—$(CH_2)_2$—$OCH_3$; $Nu_3$ is O—$(CH_2)_2$—$OCH_3$; $Nu_5$ O—$(CH_2)$; each internucleoside linkage is a phosphorothioate linkage; and the cytosine at nucleobase 2 is a 5-methylcytosine (referred to herein as anti-miR-214-1).

In certain embodiments, a modified oligonucleotide complementary to a miRNA and consisting of 22 linked nucleosides has a Formula I selected from Table 1, where each internucleoside linkage is a phosphorothioate internucleoside linkage. In certain embodiments, a modified oligonucleotide having a Formula II selected from Table 1 has the nucleobase sequence of SEQ ID NO: 3.

TABLE 1

| SEQ ID NO | $n_1$ | $n_2$ | $n_3$ | $n_4$ | $n_5$ | $Nu_1$ | $Nu_3$ | $Nu_5$ |
|---|---|---|---|---|---|---|---|---|
| 3 | 2 | 2 | 3 | 13 | 2 | 2'-MOE | 2'-MOE | 2'-MOE |
| 3 | 2 | 5 | 3 | 10 | 2 | 2'-MOE | 2'-MOE | 2'-MOE |
| 3 | 2 | 8 | 3 | 7 | 2 | 2'-MOE | 2'-MOE | 2'-MOE |
| 3 | 2 | 11 | 3 | 4 | 2 | 2'-MOE | 2'-MOE | 2'-MOE |
| 3 | 2 | 9 | 3 | 6 | 2 | 2'-MOE | 2'-MOE | 2'-MOE |
| 3 | 2 | 10 | 3 | 5 | 2 | 2'-MOE | 2'-MOE | 2'-MOE |
| 3 | 2 | 12 | 3 | 3 | 2 | 2'-MOE | 2'-MOE | 2'-MOE |
| 3 | 2 | 3 | 3 | 12 | 2 | 2'-MOE | 2'-MOE | 2'-MOE |
| 3 | 2 | 4 | 3 | 11 | 2 | 2'-MOE | 2'-MOE | 2'-MOE |
| 3 | 2 | 6 | 3 | 9 | 2 | 2'-MOE | 2'-MOE | 2'-MOE |
| 3 | 2 | 7 | 3 | 8 | 2 | 2'-MOE | 2'-MOE | 2'-MOE |
| 3 | 2 | 13 | 3 | 2 | 2 | 2'-MOE | 2'-MOE | 2'-MOE |

TABLE 1-continued

| SEQ ID NO | $n_1$ | $n_2$ | $n_3$ | $n_4$ | $n_5$ | $Nu_1$ | $Nu_3$ | $Nu_5$ |
|---|---|---|---|---|---|---|---|---|
| 3 | 2 | 8 | 6 | 4 | 2 | 2'-MOE | 2'-MOE | 2'-MOE |
| 3 | 2 | 2 | 2 | 14 | 2 | 2'-MOE | 2'-MOE | 2'-MOE |
| 3 | 2 | 3 | 2 | 13 | 2 | 2'-MOE | 2'-MOE | 2'-MOE |
| 3 | 2 | 4 | 2 | 12 | 2 | 2'-MOE | 2'-MOE | 2'-MOE |
| 3 | 2 | 5 | 2 | 11 | 2 | 2'-MOE | 2'-MOE | 2'-MOE |
| 3 | 2 | 6 | 2 | 10 | 2 | 2'-MOE | 2'-MOE | 2'-MOE |
| 3 | 2 | 7 | 2 | 9 | 2 | 2'-MOE | 2'-MOE | 2'-MOE |
| 3 | 2 | 8 | 2 | 8 | 2 | 2'-MOE | 2'-MOE | 2'-MOE |
| 3 | 2 | 9 | 2 | 7 | 2 | 2'-MOE | 2'-MOE | 2'-MOE |
| 3 | 2 | 10 | 2 | 6 | 2 | 2'-MOE | 2'-MOE | 2'-MOE |
| 3 | 2 | 11 | 2 | 5 | 2 | 2'-MOE | 2'-MOE | 2'-MOE |
| 3 | 2 | 12 | 2 | 4 | 2 | 2'-MOE | 2'-MOE | 2'-MOE |
| 3 | 2 | 13 | 2 | 3 | 2 | 2'-MOE | 2'-MOE | 2'-MOE |
| 3 | 2 | 14 | 2 | 2 | 2 | 2'-MOE | 2'-MOE | 2'-MOE |

In certain embodiments, a modified oligonucleotide complementary to a miRNA and consisting of 21 linked nucleosides has a Formula I selected from Table 2, where each internucleoside linkage is a phosphorothioate internucleoside linkage. In certain embodiments, a modified oligonucleotide having a Formula II selected from Table 2 has the nucleobase sequence of SEQ ID NO: 5.

TABLE 2

| SEQ ID NO | $n_1$ | $n_2$ | $n_3$ | $n_4$ | $n_5$ | $Nu_1$ | $Nu_3$ | $Nu_5$ |
|---|---|---|---|---|---|---|---|---|
| 4 | 2 | 2 | 2 | 13 | 2 | 2'-MOE | 2'-MOE | 2'-MOE |
| 4 | 2 | 3 | 2 | 12 | 2 | 2'-MOE | 2'-MOE | 2'-MOE |
| 4 | 2 | 4 | 2 | 11 | 2 | 2'-MOE | 2'-MOE | 2'-MOE |
| 4 | 2 | 5 | 2 | 10 | 2 | 2'-MOE | 2'-MOE | 2'-MOE |
| 4 | 2 | 6 | 2 | 9 | 2 | 2'-MOE | 2'-MOE | 2'-MOE |
| 4 | 2 | 7 | 2 | 8 | 2 | 2'-MOE | 2'-MOE | 2'-MOE |
| 4 | 2 | 8 | 2 | 7 | 2 | 2'-MOE | 2'-MOE | 2'-MOE |
| 4 | 2 | 9 | 2 | 6 | 2 | 2'-MOE | 2'-MOE | 2'-MOE |
| 4 | 2 | 10 | 2 | 5 | 2 | 2'-MOE | 2'-MOE | 2'-MOE |
| 4 | 2 | 11 | 2 | 4 | 2 | 2'-MOE | 2'-MOE | 2'-MOE |
| 4 | 2 | 12 | 2 | 3 | 2 | 2'-MOE | 2'-MOE | 2'-MOE |
| 4 | 2 | 13 | 2 | 2 | 2 | 2'-MOE | 2'-MOE | 2'-MOE |
| 4 | 2 | 2 | 3 | 12 | 2 | 2'-MOE | 2'-MOE | 2'-MOE |
| 4 | 2 | 3 | 3 | 11 | 2 | 2'-MOE | 2'-MOE | 2'-MOE |
| 4 | 2 | 4 | 3 | 10 | 2 | 2'-MOE | 2'-MOE | 2'-MOE |
| 4 | 2 | 5 | 3 | 9 | 2 | 2'-MOE | 2'-MOE | 2'-MOE |
| 4 | 2 | 6 | 3 | 8 | 2 | 2'-MOE | 2'-MOE | 2'-MOE |
| 4 | 2 | 7 | 3 | 7 | 2 | 2'-MOE | 2'-MOE | 2'-MOE |
| 4 | 2 | 8 | 3 | 6 | 2 | 2'-MOE | 2'-MOE | 2'-MOE |
| 4 | 2 | 9 | 3 | 5 | 2 | 2'-MOE | 2'-MOE | 2'-MOE |
| 4 | 2 | 10 | 3 | 4 | 2 | 2'-MOE | 2'-MOE | 2'-MOE |
| 4 | 2 | 11 | 3 | 3 | 2 | 2'-MOE | 2'-MOE | 2'-MOE |
| 4 | 2 | 12 | 3 | 2 | 2 | 2'-MOE | 2'-MOE | 2'-MOE |
| 4 | 2 | 8 | 6 | 3 | 2 | 2'-MOE | 2'-MOE | 2'-MOE |

In certain embodiments, a modified oligonucleotide complementary to a miRNA and consisting of 20 linked nucleosides has a Formula I selected from Table 3, where each internucleoside linkage is a phosphorothioate internucleoside linkage. In such certain embodiments, a modified oligonucleotide having a Formula I selected from Table 3 has the nucleobase sequence of SEQ ID NO: 6.

TABLE 3

| SEQ ID NO | n1 | n2 | n3 | n4 | n5 | Nu1 | Nu3 | Nu5 |
|---|---|---|---|---|---|---|---|---|
| 5 | 2 | 2 | 3 | 11 | 2 | 2'-MOE | 2'-MOE | 2'-MOE |
| 5 | 2 | 5 | 3 | 8 | 2 | 2'-MOE | 2'-MOE | 2'-MOE |
| 5 | 2 | 8 | 3 | 5 | 2 | 2'-MOE | 2'-MOE | 2'-MOE |
| 5 | 2 | 11 | 3 | 2 | 2 | 2'-MOE | 2'-MOE | 2'-MOE |
| 5 | 2 | 9 | 3 | 4 | 2 | 2'-MOE | 2'-MOE | 2'-MOE |

TABLE 3-continued

| SEQ ID NO | n1 | n2 | n3 | n4 | n5 | Nu1 | Nu3 | Nu5 |
|---|---|---|---|---|---|---|---|---|
| 5 | 2 | 10 | 3 | 3 | 2 | 2'-MOE | 2'-MOE | 2'-MOE |
| 5 | 2 | 3 | 3 | 10 | 2 | 2'-MOE | 2'-MOE | 2'-MOE |
| 5 | 2 | 4 | 3 | 9 | 2 | 2'-MOE | 2'-MOE | 2'-MOE |
| 5 | 2 | 6 | 3 | 7 | 2 | 2'-MOE | 2'-MOE | 2'-MOE |
| 5 | 2 | 7 | 3 | 6 | 2 | 2'-MOE | 2'-MOE | 2'-MOE |
| 5 | 2 | 8 | 6 | 2 | 2 | 2'-MOE | 2'-MOE | 2'-MOE |
| 5 | 2 | 2 | 2 | 12 | 2 | 2'-MOE | 2'-MOE | 2'-MOE |
| 5 | 2 | 3 | 2 | 11 | 2 | 2'-MOE | 2'-MOE | 2'-MOE |
| 5 | 2 | 4 | 2 | 10 | 2 | 2'-MOE | 2'-MOE | 2'-MOE |
| 5 | 2 | 5 | 2 | 9 | 2 | 2'-MOE | 2'-MOE | 2'-MOE |
| 5 | 2 | 6 | 2 | 8 | 2 | 2'-MOE | 2'-MOE | 2'-MOE |
| 5 | 2 | 7 | 2 | 7 | 2 | 2'-MOE | 2'-MOE | 2'-MOE |
| 5 | 2 | 8 | 2 | 6 | 2 | 2'-MOE | 2'-MOE | 2'-MOE |
| 5 | 2 | 9 | 2 | 5 | 2 | 2'-MOE | 2'-MOE | 2'-MOE |
| 5 | 2 | 10 | 2 | 4 | 2 | 2'-MOE | 2'-MOE | 2'-MOE |
| 5 | 2 | 11 | 2 | 3 | 2 | 2'-MOE | 2'-MOE | 2'-MOE |
| 5 | 2 | 12 | 2 | 2 | 2 | 2'-MOE | 2'-MOE | 2'-MOE |

In certain embodiments, a modified oligonucleotide complementary to a miRNA and consisting of 22 linked nucleosides has a Formula I selected from Table 4, where each internucleoside linkage is a phosphorothioate internucleoside linkage. In certain embodiments, a modified oligonucleotide having a Formula I selected from Table 1 comprises a nucleobase sequence selected from among SEQ ID NOs 3, 4, 5, 6, 7, 8, 9, 10, 11, 12, 13, 16, 17, 18, 20, 22, 24, 26, 28, and 30.

TABLE 4

| $n_1$ | $n_2$ | $n_3$ | $n_4$ | $n_5$ | $Nu_1$ | $Nu_3$ | $Nu_5$ |
|---|---|---|---|---|---|---|---|
| 2 | 2 | 3 | 13 | 2 | 2'-MOE | 2'-MOE | 2'-MOE |
| 2 | 5 | 3 | 10 | 2 | 2'-MOE | 2'-MOE | 2'-MOE |
| 2 | 8 | 3 | 7 | 2 | 2'-MOE | 2'-MOE | 2'-MOE |
| 2 | 11 | 3 | 4 | 2 | 2'-MOE | 2'-MOE | 2'-MOE |
| 2 | 9 | 3 | 6 | 2 | 2'-MOE | 2'-MOE | 2'-MOE |
| 2 | 10 | 3 | 5 | 2 | 2'-MOE | 2'-MOE | 2'-MOE |
| 2 | 12 | 3 | 3 | 2 | 2'-MOE | 2'-MOE | 2'-MOE |
| 2 | 3 | 3 | 12 | 2 | 2'-MOE | 2'-MOE | 2'-MOE |
| 2 | 4 | 3 | 11 | 2 | 2'-MOE | 2'-MOE | 2'-MOE |
| 2 | 6 | 3 | 9 | 2 | 2'-MOE | 2'-MOE | 2'-MOE |
| 2 | 7 | 3 | 8 | 2 | 2'-MOE | 2'-MOE | 2'-MOE |
| 2 | 13 | 3 | 2 | 2 | 2'-MOE | 2'-MOE | 2'-MOE |
| 2 | 8 | 6 | 4 | 2 | 2'-MOE | 2'-MOE | 2'-MOE |
| 2 | 2 | 2 | 14 | 2 | 2'-MOE | 2'-MOE | 2'-MOE |
| 2 | 3 | 2 | 13 | 2 | 2'-MOE | 2'-MOE | 2'-MOE |
| 2 | 4 | 2 | 12 | 2 | 2'-MOE | 2'-MOE | 2'-MOE |
| 2 | 5 | 2 | 11 | 2 | 2'-MOE | 2'-MOE | 2'-MOE |
| 2 | 6 | 2 | 10 | 2 | 2'-MOE | 2'-MOE | 2'-MOE |
| 2 | 7 | 2 | 9 | 2 | 2'-MOE | 2'-MOE | 2'-MOE |
| 2 | 8 | 2 | 8 | 2 | 2'-MOE | 2'-MOE | 2'-MOE |
| 2 | 9 | 2 | 7 | 2 | 2'-MOE | 2'-MOE | 2'-MOE |
| 2 | 10 | 2 | 6 | 2 | 2'-MOE | 2'-MOE | 2'-MOE |
| 2 | 11 | 2 | 5 | 2 | 2'-MOE | 2'-MOE | 2'-MOE |
| 2 | 12 | 2 | 4 | 2 | 2'-MOE | 2'-MOE | 2'-MOE |
| 2 | 13 | 2 | 3 | 2 | 2'-MOE | 2'-MOE | 2'-MOE |
| 2 | 14 | 2 | 2 | 2 | 2'-MOE | 2'-MOE | 2'-MOE |

In certain embodiments, a modified oligonucleotide complementary to a miRNA and consisting of 23 linked nucleosides has a Formula I selected from Table 5, where each internucleoside linkage is a phosphorothioate internucleoside linkage. In certain embodiments, a modified oligonucleotide having a Formula I selected from Table 5 comprises a nucleobase sequence selected from among SEQ ID NOs 3, 4, 5, 6, 7, 8, 9, 10, 11, 12, 13, 16, 17, 18, 20, 22, 24, 26, 28, and 30.

TABLE 5

| n1 | n2 | n3 | n4 | n5 | Nu1 | Nu3 | Nu5 |
|---|---|---|---|---|---|---|---|
| 2 | 2 | 3 | 14 | 2 | 2'-MOE | 2'-MOE | 2'-MOE |
| 2 | 5 | 3 | 11 | 2 | 2'-MOE | 2'-MOE | 2'-MOE |
| 2 | 8 | 3 | 8 | 2 | 2'-MOE | 2'-MOE | 2'-MOE |
| 2 | 11 | 3 | 5 | 2 | 2'-MOE | 2'-MOE | 2'-MOE |
| 2 | 14 | 3 | 2 | 2 | 2'-MOE | 2'-MOE | 2'-MOE |
| 2 | 9 | 3 | 7 | 2 | 2'-MOE | 2'-MOE | 2'-MOE |
| 2 | 10 | 3 | 6 | 2 | 2'-MOE | 2'-MOE | 2'-MOE |
| 2 | 12 | 3 | 4 | 2 | 2'-MOE | 2'-MOE | 2'-MOE |
| 2 | 3 | 3 | 13 | 2 | 2'-MOE | 2'-MOE | 2'-MOE |
| 2 | 4 | 3 | 12 | 2 | 2'-MOE | 2'-MOE | 2'-MOE |
| 2 | 6 | 3 | 10 | 2 | 2'-MOE | 2'-MOE | 2'-MOE |
| 2 | 7 | 3 | 9 | 2 | 2'-MOE | 2'-MOE | 2'-MOE |
| 2 | 13 | 3 | 3 | 2 | 2'-MOE | 2'-MOE | 2'-MOE |
| 2 | 8 | 6 | 5 | 2 | 2'-MOE | 2'-MOE | 2'-MOE |
| 2 | 2 | 2 | 15 | 2 | 2'-MOE | 2'-MOE | 2'-MOE |
| 2 | 3 | 2 | 14 | 2 | 2'-MOE | 2'-MOE | 2'-MOE |
| 2 | 4 | 2 | 13 | 2 | 2'-MOE | 2'-MOE | 2'-MOE |
| 2 | 5 | 2 | 12 | 2 | 2'-MOE | 2'-MOE | 2'-MOE |
| 2 | 6 | 2 | 11 | 2 | 2'-MOE | 2'-MOE | 2'-MOE |
| 2 | 7 | 2 | 10 | 2 | 2'-MOE | 2'-MOE | 2'-MOE |
| 2 | 8 | 2 | 9 | 2 | 2'-MOE | 2'-MOE | 2'-MOE |
| 2 | 9 | 2 | 8 | 2 | 2'-MOE | 2'-MOE | 2'-MOE |
| 2 | 10 | 2 | 7 | 2 | 2'-MOE | 2'-MOE | 2'-MOE |
| 2 | 11 | 2 | 6 | 2 | 2'-MOE | 2'-MOE | 2'-MOE |
| 2 | 12 | 2 | 5 | 2 | 2'-MOE | 2'-MOE | 2'-MOE |
| 2 | 13 | 2 | 4 | 2 | 2'-MOE | 2'-MOE | 2'-MOE |

In certain embodiments, a modified oligonucleotide complementary to a miRNA and consisting of 24 linked nucleosides has a Formula I selected from Table 6, where each internucleoside linkage is a phosphorothioate internucleoside linkage. In certain embodiments, a modified oligonucleotide having a Formula I selected from Table 6 comprises a nucleobase sequence selected from among SEQ ID NOs 3, 4, 5, 6, 7, 8, 9, 10, 11, 12, 13, 16, 17, 18, 20, 22, 24, 26, 28, and 30.

TABLE 6

| $n_1$ | $n_2$ | $n_3$ | $n_4$ | $n_5$ | $Nu_1$ | $Nu_3$ | $Nu_5$ |
|---|---|---|---|---|---|---|---|
| 2 | 2 | 2 | 16 | 2 | 2'-MOE | 2'-MOE | 2'-MOE |
| 2 | 3 | 2 | 15 | 2 | 2'-MOE | 2'-MOE | 2'-MOE |
| 2 | 4 | 2 | 14 | 2 | 2'-MOE | 2'-MOE | 2'-MOE |
| 2 | 5 | 2 | 13 | 2 | 2'-MOE | 2'-MOE | 2'-MOE |
| 2 | 6 | 2 | 12 | 2 | 2'-MOE | 2'-MOE | 2'-MOE |
| 2 | 7 | 2 | 11 | 2 | 2'-MOE | 2'-MOE | 2'-MOE |
| 2 | 8 | 2 | 10 | 2 | 2'-MOE | 2'-MOE | 2'-MOE |
| 2 | 9 | 2 | 9 | 2 | 2'-MOE | 2'-MOE | 2'-MOE |
| 2 | 10 | 2 | 8 | 2 | 2'-MOE | 2'-MOE | 2'-MOE |
| 2 | 11 | 2 | 7 | 2 | 2'-MOE | 2'-MOE | 2'-MOE |
| 2 | 12 | 2 | 6 | 2 | 2'-MOE | 2'-MOE | 2'-MOE |
| 2 | 13 | 2 | 5 | 2 | 2'-MOE | 2'-MOE | 2'-MOE |
| 2 | 14 | 2 | 4 | 2 | 2'-MOE | 2'-MOE | 2'-MOE |
| 2 | 15 | 2 | 3 | 2 | 2'-MOE | 2'-MOE | 2'-MOE |
| 2 | 16 | 2 | 2 | 2 | 2'-MOE | 2'-MOE | 2'-MOE |
| 2 | 2 | 3 | 15 | 2 | 2'-MOE | 2'-MOE | 2'-MOE |
| 2 | 3 | 3 | 14 | 2 | 2'-MOE | 2'-MOE | 2'-MOE |
| 2 | 4 | 3 | 13 | 2 | 2'-MOE | 2'-MOE | 2'-MOE |
| 2 | 5 | 3 | 12 | 2 | 2'-MOE | 2'-MOE | 2'-MOE |
| 2 | 6 | 3 | 11 | 2 | 2'-MOE | 2'-MOE | 2'-MOE |
| 2 | 7 | 3 | 10 | 2 | 2'-MOE | 2'-MOE | 2'-MOE |
| 2 | 8 | 3 | 9 | 2 | 2'-MOE | 2'-MOE | 2'-MOE |
| 2 | 9 | 3 | 8 | 2 | 2'-MOE | 2'-MOE | 2'-MOE |
| 2 | 10 | 3 | 7 | 2 | 2'-MOE | 2'-MOE | 2'-MOE |
| 2 | 11 | 3 | 6 | 2 | 2'-MOE | 2'-MOE | 2'-MOE |
| 2 | 12 | 3 | 5 | 2 | 2'-MOE | 2'-MOE | 2'-MOE |
| 2 | 13 | 3 | 4 | 2 | 2'-MOE | 2'-MOE | 2'-MOE |
| 2 | 14 | 3 | 3 | 2 | 2'-MOE | 2'-MOE | 2'-MOE |
| 2 | 15 | 3 | 2 | 2 | 2'-MOE | 2'-MOE | 2'-MOE |
| 2 | 8 | 6 | 6 | 2 | 2'-MOE | 2'-MOE | 2'-MOE |

In certain embodiments, a modified oligonucleotide having a positionally modified motif comprises LNA. In certain embodiments, a modified oligonucleotide has a motif selected from among one of the motifs listed below, wherein L=an LNA nucleoside, d=a DNA nucleoside, M=a 2'-MOE nucleoside, and F=a 2'-Fluoro nucleoside. In certain embodiments, nucleosides in parentheses are optionally included in the modified oligonucleotide, in other words, the motif encompasses modified oligonucleotides of varying lengths depending upon how many nucleosides in parentheses are included.

LdLddLLddLdLdLL
Ld Ld LLLd d LLLd LL
LMLMMLLMMLMLMLL
LMLMLLLMMLLLMLL
LFLFFLLFFLFLFLL
LFLFLLLFFLLLFLL
LddLddLddL(d)(d)(L)(d)(d)(L)(d)
dLddLddLdd(L)(d)(d)(L)(d)(d)(L)
ddLddLddLd(d)(L)(d)(d)(L)(d)(d)
LMMLMMLMML(M)(M)(L)(M)(M)(L)(M)
MLMMLMMLMM(L)(M)(M)(L)(M)(M)(L)
MMLMMLMMLM(M)(L)(M)(M)(M)(L)(M)(M)
LFFLFFLFFL(F)(F)(L)(F)(F)(L)(F)
FLFFLFFLFF(L)(F)(F)(L)(F)(F)(L)
FFLFFLFFLF(F)(L)(F)(F)(L)(F)(F)
dLdLdLdLdL(d)(L)(d)(L)(d)(L)(d)
LdLdLdLdLdL(d)(L)(d)(L)(d)(L)(d)(L)
MLMLMLMLML(M)(L)(M)(L)(M)(L)(M)
LMLMLMLMLML(M)(L)(M)(L)(M)(L)(M)(L)
FLFLFLFLFL(F)(L)(F)(L)(F)(L)(F)
LFLFLFLFLFL(F)(L)(F)(L)(F)(L)(F)(L)

Additional motifs are disclosed in PCT Publication No. WO 2007/112754, which is herein incorporated by reference in its entirety for the description of oligonucleotide modifications and patterns of oligonucleotide modifications, including but not limited to the description of LNA-containing oligonuleotides.

A modified oligonucleotide consisting of 6 to 12 linked nucleosides may comprise LNA modifications at certain positions. In certain embodiments, a modified oligonucleotide consisting of 6 to 12 linked nucleosides comprises a LNA modification at each nucleoside. In certain embodiments, at least 50% of the nucleosides of a modified oligonucleotide of 6 to 12 nucleosides in length comprise an LNA modification. In certain embodiments, at least 60% of the nucleosides of a modified oligonucleotide of 6 to 12 nucleosides in length comprise an LNA modification. In certain embodiments, at least 70% of the nucleosides of a modified oligonucleotide of 6 to 12 nucleosides in length comprise an LNA modification. In certain embodiments, at least 80% of the nucleosides of a modified oligonucleotide of 6 to 12 nucleosides in length comprise an LNA modification. In certain embodiments, at least 90% of the nucleosides of a modified oligonucleotide of 6 to 12 nucleosides in length comprise an LNA modification. In certain embodiments, a modified oligonucleotide complementary to the seed sequence of miR-214 comprises an LNA modification at each nucleoside of the seed match sequence. Additional motifs are described in PCT Publication No. WO 2009/043353, which is herein incorporated by reference in its entirety for the description of modified oligonucleotides complementary to microRNA, that are 6 to 12 nucleosides in length.

A modified oligonucleotide having a gapmer motif may have an internal region consisting of linked 2'-deoxynucleotides, and external regions consisting of linked 2'-modified nucleosides. Such a gapmer may be designed to elicit RNase H cleavage of a miRNA precursor. The internal 2'-deoxynucleoside region serves as a substrate for RNase H, allowing the cleavage of the miRNA precursor to which a modified oligonucleotide is targeted. In certain embodiments, each nucleoside of each external region comprises the same 2'-modified nucleoside. In certain embodiments, one external region is uniformly comprised of a first 2'-modified nucleoside and the other external region is uniformly comprised of a second 2'-modified nucleoside.

A modified oligonucleotide having a gapmer motif may have a sugar modification at each nucleoside. In certain embodiments, the internal region is uniformly comprised of a first 2'-modified nucleoside and each of the wings is uniformly comprised of a second 2'-modified nucleoside. In certain such embodiments, the internal region is uniformly comprised of 2'-fluoro nucleosides and each external region is uniformly comprised of 2'-O-methoxyethyl nucleosides.

In certain embodiments, each external region of a gapmer consists of linked 2'-O-methoxyethyl nucleosides. In certain embodiments, each external region of a gapmer consists of linked 2'-O-methyl nucleosides. In certain embodiments, each external region of a gapmer consists of 2'-fluoro nucleosides. In certain embodiments, each external region of a gapmer consists of linked bicyclic nucleosides.

In certain embodiments, each nucleoside of one external region of a gapmer comprises 2'-O-methoxyethyl nucleosides and each nucleoside of the other external region comprises a different 2'-modification. In certain such embodiments, each nucleoside of one external region of a gapmer comprises 2'-O-methoxyethyl nucleosides and each nucleoside of the other external region comprises 2'-O-methyl nucleosides. In certain such embodiments, each nucleoside of one external region of a gapmer comprises 2'-O-methoxyethyl nucleosides and each nucleoside of the other external region comprises 2'-fluoro nucleosides. In certain such embodiments, each nucleoside of one external region of a gapmer comprises 2'-O-methyl nucleosides and each nucleoside of the other external region comprises 2'-fluoro nucleosides. In certain such embodiments, each nucleoside of one external region of a gapmer comprises 2'-O-methoxyethyl nucleosides and each nucleoside of the other external region comprises bicyclic nucleosides. In certain such embodiments, each nucleoside of one external region of a gapmer comprises 2'-O-methyl nucleosides and each nucleoside of the other external region comprises bicyclic nucleosides.

In certain embodiments, nucleosides of one external region comprise two or more sugar modifications. In certain embodiments, nucleosides of each external region comprise two or more sugar modifications. In certain embodiments, at least one nucleoside of an external region comprises a 2'-O-methoxyethyl sugar and at least one nucleoside of the same external region comprises a 2'-fluoro sugar. In certain embodiments, at least one nucleoside of an external region comprises a 2'-O-methoxyethyl sugar and at least one nucleoside of the same external region comprises a bicyclic sugar moiety. In certain embodiments, at least one nucleoside of an external region comprises a 2'-methyl sugar and at least one nucleoside of the same external region comprises a bicyclic sugar moiety. In certain embodiments at least one nucleoside of an external region comprises a 2'-O-methyl sugar and at least one nucleoside of the same external region comprises a 2'-fluoro sugar. In certain embodiments, at least one nucleoside of an external region comprises a 2'-fluoro sugar and at least one nucleoside of the same external region comprises a bicyclic sugar moiety.

In certain embodiments, each external region of a gapmer consists of the same number of linked nucleosides. In certain embodiments, one external region of a gapmer consists a number of linked nucleosides different than that of the other external region.

In certain embodiments, the external regions comprise, independently, from 1 to 6 nucleosides. In certain embodiments, an external region comprises 1 nucleoside. In certain embodiments, an external region comprises 2 nucleosides. In certain embodiments, an external region comprises 3 nucleosides. In certain embodiments, an external region comprises 4 nucleosides. In certain embodiments, an external region comprises 5 nucleosides. In certain embodiments, an external region comprises 6 nucleosides. In certain embodiments, the internal region consists of 17 to 28 linked nucleosides. In certain embodiments, an internal region consists of 17 to 21 linked nucleosides. In certain embodiment, an internal region consists of 17 linked nucleosides. In certain embodiments, an internal region consists of 18 linked nucleosides. In certain embodiments, an internal region consists of 19 linked nucleosides. In certain embodiments, an internal region consists of 20 linked nucleosides. In certain embodiments, an internal region consists of 21 linked nucleosides. In certain embodiments, an internal region consists of 22 linked nucleosides. In certain embodiments, an internal region consists of 23 linked nucleosides. In certain embodiments, an internal region consists of 24 linked nucleosides. In certain embodiments, an internal region consists of 25 linked nucleosides. In certain embodiments, an internal region consists of 26 linked nucleosides. In certain embodiments, an internal region consists of 27 linked nucleosides. In certain embodiments, an internal region consists of 28 linked nucleosides.

Certain Pharmaceutical Compositions

Provided herein are pharmaceutical compositions comprising oligonucleotides. In certain embodiments, such pharmaceutical compositions are used for the treatment of fibrotic disorders, and associated conditions. In certain embodiments, a pharmaceutical composition provided herein comprises a compound comprising a modified oligonucleotide consisting of 8 to 30 linked nucleosides and having a nucleobase sequence complementary to miR-214, or a precursor thereof. In certain embodiments, a pharmaceutical composition provided herein comprises a compound consisting of a modified oligonucleotide consisting of 8 to 30 linked nucleosides and having a nucleobase sequence complementary to miR-214, or a precursor thereof.

Suitable administration routes include, but are not limited to, oral, rectal, transmucosal, intestinal, enteral, topical, suppository, through inhalation, intrathecal, intraventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the liver).

In certain embodiments, a pharmaceutical composition is administered in the form of a dosage unit (e.g., tablet, capsule, bolus, etc.). In certain embodiments, such pharmaceutical compositions comprise an oligonucleotide in a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, a pharmaceutical composition of the comprises a dose of modified oligonucleotide selected from 25 mg, 50 mg, 75 mg, 100 mg, 150 mg, 200 mg, 250 mg, 300 mg, 350 mg, 400 mg, 500 mg, 600 mg, 700 mg, and 800 mg.

In certain embodiments, a pharmaceutical agent is sterile lyophilized modified oligonucleotide that is reconstituted with a suitable diluent, e.g., sterile water for injection or sterile saline for injection. The reconstituted product is administered as a subcutaneous injection or as an intravenous infusion after dilution into saline. The lyophilized drug product consists of an oligonucleotide which has been prepared in water for injection, or in saline for injection, adjusted to pH 7.0-9.0 with acid or base during preparation, and then lyophilized. The lyophilized modified oligonucleotide may be 25-800 mg of an oligonucleotide. It is understood that this encompasses 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of modified lyophilized oligonucleotide. The lyophilized drug product may be packaged in a 2 mL Type I, clear glass vial (ammonium sulfate-treated), stoppered with a bromobutyl rubber closure and sealed with an aluminum FLIP-OFF® overseal.

In certain embodiments, the pharmaceutical compositions provided herein may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

Lipid moieties have been used in nucleic acid therapies in a variety of methods. In one method, the nucleic acid is introduced into preformed liposomes or lipoplexes made of mixtures of cationic lipids and neutral lipids. In another method, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, INTRALIPID is used to prepare a pharmaceutical composition comprising an oligonucleotide. Intralipid is fat emulsion prepared for intravenous administration. It is made up of 10% soybean oil, 1.2% egg yolk phospholipids, 2.25% glycerin, and water for injection. In addition, sodium hydroxide has been added to adjust the pH so that the final product pH range is 6 to 8.9.

In certain embodiments, a pharmaceutical composition provided herein comprise a polyamine compound or a lipid moiety completed with a nucleic acid. In certain embodiments, such preparations comprise one or more compounds each individually having a structure defined by formula (I) or a pharmaceutically acceptable salt thereof,

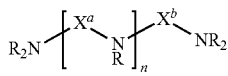

wherein each $X^a$ and $X^b$, for each occurrence, is independently $C_{1-6}$ alkylene; n is 0, 1, 2, 3, 4, or 5; each R is independently H, wherein at least n+2 of the R moieties in at least about 80% of the molecules of the compound of formula (I) in the preparation are not H; m is 1, 2, 3 or 4; Y is O, $NR^2$, or S; $R^1$ is alkyl, alkenyl, or alkynyl; each of which is optionally substituted with one or more substituents; and $R^2$ is H, alkyl, alkenyl, or alkynyl; each of which is optionally substituted each of which is optionally substituted with one or more substituents; provided that, if n=0, then at least n+3 of the R moieties are not H. Such preparations are described in PCT publication WO 2008/042973, which is herein incorporated by reference in its entirety for the disclosure of lipid preparations. Certain additional preparations are described in Akinc et al., *Nature Biotechnology* 26, 561-569 (1 May 2008), which is herein incorporated by reference in its entirety for the disclosure of lipid preparations.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein is prepared using known techniques, including, but not limited to mixing, dissolving, granulating, dragee-making, levigating, emulsifying, encapsulating, entrapping or tabletting processes.

In certain embodiments, a pharmaceutical composition provided herein is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition provided herein is a solid (e.g., a powder, tablet, and/or capsule). In certain of such embodiments, a solid pharmaceutical composition comprising one or more oligonucleotides is prepared using ingredients known in the art, including, but not limited to, starches, sugars, diluents, granulating agents, lubricants, binders, and disintegrating agents.

In certain embodiments, a pharmaceutical composition provided herein is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied; for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein comprises a sustained-release system. A non-limiting example of such a sustained-release system is a semipermeable matrix of solid hydrophobic polymers. In certain embodiments, sustained-release systems may, depending on their chemical nature, release pharmaceutical agents over a period of hours, days, weeks or months.

In certain embodiments, a pharmaceutical composition provided herein is prepared for oral administration. In certain of such embodiments, a pharmaceutical composition is formulated by combining one or more compounds comprising an oligonucleotide with one or more pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. In certain embodiments, pharmaceutical compositions for oral use are obtained by mixing oligonucleotide and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In certain embodiments, a pharmaceutical composition is prepared for rectal administration, such as a suppositories or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotides provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

Certain Kits

The present invention also provides kits. In some embodiments, the kits comprise one or more compounds of the invention comprising a modified oligonucleotide, wherein the nucleobase sequence of the oligonucleotide is complementary to miR-214. The compounds complementary to miR-214 can be any of the compounds described herein, and can have any of the modifications described herein. In some embodiments, the compounds complementary to miR-214 can be present within a vial. A plurality of vials, such as 10, can be present in, for example, dispensing packs. In some embodiments, the vial is manufactured so as to be accessible with a syringe. The kit can also contain instructions for using the compounds complementary to miR-214.

In some embodiments, the kits may be used for administration of the compound complementary to miR-214 to a subject. In such instances, in addition to compounds complementary to miR-214, the kit can further comprise one or more of the following: syringe, alcohol swab, cotton ball, and/or gauze pad. In some embodiments, the compounds complementary to miR-214 can be present in a pre-filled syringe (such as a single-dose syringes with, for example, a 27 gauge, ½ inch needle with a needle guard), rather than in a vial. A plurality of pre-filled syringes, such as 10, can be present in, for example, dispensing packs. The kit can also contain instructions for administering the compounds complementary to miR-214.

Certain Experimental Models

In certain embodiments, the present invention provides methods of using and/or testing modified oligonucleotides of the present invention in an experimental model. Those having skill in the art are able to select and modify the protocols for such experimental models to evaluate a pharmaceutical agent of the invention.

Generally, modified oligonucleotides are first tested in cultured cells. Suitable cell types include those that are related to the cell type to which delivery of an oligonucleotide is desired in vivo. For example, suitable cell types for the study of the methods described herein include primary or cultured cardiac fibroblasts and cardiomyocytes.

In certain embodiments, the extent to which an oligonucleotide interferes with the activity of a miRNA is assessed in cultured cells. In certain embodiments, inhibition of miRNA activity may be assessed by measuring the levels of the miRNA. Alternatively, the level of a predicted or validated miRNA target may be measured. An inhibition of miRNA activity may result in the increase in the mRNA and/or protein of a miRNA target. Further, in certain embodiments, certain phenotypic outcomes may be measured.

Suitable experimental animal models for the testing of the methods described herein include but are not limited to a pressure overload-induced hypertrophy, an isoproterenol-induced cardiac hypertrophy model, an exercise-induced cardiac hypertrophy model, a high-salt diet-induced cardiac hypertrophy model, and a hormone-induced cardiac hypertrophy model.

Suitable experimental models of kidney fibrosis in mice or rats include progressive glomerulonephritis from anti-glomerular basement membrane disease, Alport syndrome, or spontaneous lupus nephritis, and NOD or db/db nephritic mice (models for diabetic nephropathy), all of which chronically progress at a slow pace, and unilateral ureteral obstruction.

Certain Quantitation Assays

The effects of antisense inhibition of a miRNA following the administration of modified oligonucleotides may be assessed by a variety of methods known in the art. In certain embodiments, these methods are be used to quantitate miRNA levels in cells or tissues in vitro or in vivo. In certain embodiments, changes in miRNA levels are measured by microarray analysis. In certain embodiments, changes in miRNA levels are measured by one of several commercially available PCR assays, such as the TaqMan® MicroRNA Assay (Applied Biosystems). In certain embodiments, antisense inhibition of a miRNA is assessed by measuring the mRNA and/or protein level of a target of a miRNA. Antisense inhibition of a miRNA generally results in the increase in the level of mRNA and/or protein of a target of the miRNA.

Target Engagement Assay

Modulation of microRNA activity with an anti-miR or microRNA mimic may be assessed by measuring target engagement. In certain embodiments, target engagement is measured by microarray profiling of mRNAs. The sequences of the mRNAs that are modulated (either increased or decreased) by the anti-miR or microRNA mimic are searched for microRNA seed sequences, to compare modulation of mRNAs that are targets of the miRNA to modulation of mRNAs that are not targets of the miRNA. In this manner, the interaction of the anti-miR with a miRNA, or a miRNA mimic with its targets, can be evaluated. In the case of an anti-miR, mRNAs whose expression levels are increased are screened for the mRNA sequences that comprise a seed match to the miRNA to which the anti-miR is complementary.

The following examples are presented in order to more fully illustrate some embodiments of the invention. They should, in no way be construed, however, as limiting the broad scope of the invention.

EXAMPLES

Example 1

MicroRNA Expression in Kidney Fibrosis Samples

Unilateral ureteral obstruction (UUO) is a well-established experimental model of renal injury leading to interstitial fibrosis, and thus is used as an experimental model that is reflective of human kidney disease. UUO is induced by surgically ligating a single ureter. As fibrosis is characterized by an increase in collagen, the presence and extent of kidney fibrosis may be determined by measuring collagen content. Kidney fibrosis may be visualized by staining tissue samples with picro-sirius red to detect increases in collagen content. Kidney fibrosis may also be observed by measuring the amount of hydroxyproline, which is a major component of collagen, in a sample.

To identify microRNAs that are dysregulated in kidney fibrosis, microRNA profiling was performed on RNA isolated from either normal kidney or obstructed kidney. Obstructed kidney was confirmed by increased collagen content, as evidenced by increases in picro-siruis red staining and hydroxyproline. It was found that miR-214 was upregulated approximately 8-fold compared to normal kidney. When measured in distinct cell types of the kidney, miR-214 was found to be strongly upregulated in pericytes (approximately 10-fold 2 days following obstruction and approximately 6-fold 7 days following obstruction), which are considered to be the fibrogenic cells that contribute to kidney fibrosis (Table 7).

Accordingly, miR-214 is a target for the treatment, prevention, and/or amelioration of fibrosis, including but not limited to kidney fibrosis.

TABLE 7

Effect of kidney fibrosis in the UUO model on miR-214 upregulation (%) in distinct kidney cells

| Days following obstruction | Endothelial cells | Pericytes | Macrophages | Epithelial cells |
|---|---|---|---|---|
| 2 | +74 | +866 | −45 | −59 |
| 7 | +183 | +530 | +460 | +194 |

An additional experimental model of kidney fibrosis is the ischemia reperfusion model, in which a period of ischemia is followed by a period of reperfusion, resulting in both functional and structural damage to the kidneys.

RNA was isolated from kidney subjected to ischemia and reperfusion. Consistent with miR-214 expression from the UUO kidney sample, miR-214 was found to be upregulated approximately 7-fold compared to sham-operated kidney on day 10 following reperfusion (Table 8).

TABLE 8

Effect of kidney fibrosis in the ischemic/reperfusion model on miR-214 upregulation (%)

| Days following obstruction | % miR-214 |
|---|---|
| 2 | +390 |
| 10 | +606 |

Example 2

Inhibition of MiR-214 Attenuates Kidney Fibrosis

Anti-miR targeting miR-214 was evaluated in the UUO model of kidney fibrosis. In this study, the anti-miR used was anti-miR-214-1, which is a modified oligonucleotide consisting of 22 linked nucleosides; has the nucleobase sequence of SEQ ID NO: 3; nucleosides 1, 2, 12, 13, 14, 21, and 22 are 2'-O-methoxyethyl nucleosides; nucleosides 3 through 11 and 15 through 20 are 2'-fluoro nucleosides; each internucleoside linkage is a phosphorothioate linkage; and the cytosine at position 2 is a 5-methylcytosine (herein referred to as anti-miR-214-1). The control anti-miR used was a modified oligonucleotide consisting of 22 linked nucleosides, nucleosides 1, 2, 12, 13, 14, 21, and 22 are 2'-O-methoxyethyl nucleosides; nucleosides 3 through 11 and 15 through 20 are 2'-fluoro nucleosides; each internucleoside linkage is a phosphorothioate linkage; and the cytosine at position 2 is a 5-methylcytosine (herein referred to as control anti-miR).

In one experiment, anti-miR was administered at Day −5, Day −2, and Day 3 of the study. Treatment groups included: (1) sham surgery, in which the ureter is exposed and manipulated, but not ligated; (2) UUO surgery treated with PBS; (3) UUO surgery treated with 20 mg/kg control anti-miR; (4) UUO surgery treated with 20 mg/kg anti-miR-214-1. PBS or anti-miR was administered intraperitoneally at Day 5 and Day 2 prior to UUO surgery. The day of UUO or sham surgery was Day 0. Anti-miR-214, control anti-miR, or saline was administered to UUO-treated mice on Day 3 following UUO surgery. Kidney tissue was harvested from all groups on Day 10 following surgery. Kidney tissue was analyzed for hydroxyproline content.

Measurement of hydroxyproline content revealed a significant reduction in mice that underwent UUO surgery and received anti-miR-214-1, compared to mice that underwent UUO surgery and received control anti-miR (Table 9).

TABLE 9

Effect of antisense inhibition of miR-214 in the UUO model on hydroxyproline content

| Groups | Animal# | Hydroxyproline (μg/mg dry tissue) | Average content |
|---|---|---|---|
| Sham | 1 | 1.9 | 2.0 |
|  | 2 | 2.2 |  |
|  | 3 | 2.1 |  |
|  | 4 | 2.0 |  |
| UUO + PBS | 1 | 5.8 | 5.7 |
|  | 2 | 7.0 |  |
|  | 3 | 6.1 |  |
|  | 4 | 7.9 |  |
|  | 5 | 5.2 |  |
|  | 6 | 2.5 |  |
|  | 7 | 5.4 |  |
| UUO + control anti-miR | 1 | 7.3 | 6.1 |
|  | 2 | 7.9 |  |
|  | 3 | 6.2 |  |
|  | 4 | 6.0 |  |
|  | 5 | 6.5 |  |
|  | 6 | 5.5 |  |
|  | 7 | 5.6 |  |
|  | 8 | 4.2 |  |
| UUO + anti-miR-214 | 1 | 5.7 | 4.9 |
|  | 2 | 6.4 | ($p < 0.05$ vs UUO + PBS) |
|  | 3 | 4.1 |  |
|  | 4 | 4.9 |  |
|  | 5 | 5.2 |  |
|  | 6 | 5.0 |  |
|  | 7 | 4.0 |  |
|  | 8 | 3.9 |  |

In another experiment, anti-miR was administered at Day −4, Day −1, and Day 3 of the study. Treatment groups included: (1) sham surgery, in which the ureter is exposed and manipulated, but not ligated; (2) UUO surgery treated with PBS; (3) UUO surgery treated with 20 mg/kg control anti-miR; (4) UUO surgery treated with 20 mg/kg anti-miR-214-1. PBS or anti-miR was administered intraperitoneally at Day 4 and Day 1 prior to UUO surgery. The day of UUO or sham surgery was Day 0. Anti-miR-214, control anti-miR, or saline was administered to UUO-treated mice on Day 3 following UUO surgery. Kidney tissue was harvested from all groups on Day 10 following surgery. Kidney tissue was prepared for histological analysis by picro-sirius red staining, and was analyzed for hydroxyproline content.

Measurement of hydroxyproline content revealed a significant reduction in mice that underwent UUO surgery and received anti-miR-214-1, compared to mice that underwent UUO surgery and received control anti-miR (Table 10).

TABLE 10

Effect of antisense inhibition of miR-214 in the UUO model on hydroxyproline content

| Groups | Animal# | Hydroxyproline (μg/mg dry tissue) | Average content |
|---|---|---|---|
| Sham | 1 | 2.1 | 2.2 |
|  | 2 | 2.3 |  |
|  | 3 | 2.0 |  |
|  | 4 | 2.2 |  |
|  | 5 | 2.3 |  |
|  | 6 | 2.3 |  |
| UUO + PBS | 1 | 7.5 | 6.6 |
|  | 2 | 10.1 |  |
|  | 3 | 5.2 |  |

TABLE 10-continued

Effect of antisense inhibition of miR-214 in the UUO model on hydroxyproline content

| Groups | Animal# | Hydroxyproline (µg/mg dry tissue) | Average content |
|---|---|---|---|
| | 4 | 6.7 | |
| | 5 | 6.6 | |
| | 6 | 3.7 | |
| UUO + control anti-miR | 1 | 7.1 | 6.3 |
| | 2 | 5.6 | |
| | 3 | 4.3 | |
| | 4 | 5.9 | |
| | 5 | 8.9 | |
| | 6 | 6.0 | |
| UUO + anti-miR-214 | 1 | 2.8 | 4.3 |
| | 2 | 3.7 | (p < 0.0001 vs |
| | 3 | 4.9 | UUO + PBS) |
| | 4 | 4.0 | |
| | 5 | 5.4 | |
| | 6 | 5.1 | |

Collagen content was quantitated by pico-sirius fed staining (Table 11). The increase in collagen content is a measure of fibrosis and was observed to be reduced after anti-miR-214 treatment.

TABLE 11

Effect of antisense inhibition of miR-214 in the UUO model on collagen content

| Groups | Section# | Collagen area fraction (%) | Average content |
|---|---|---|---|
| Sham | 1 | 6.5 | 5.0 |
| | 2 | 4.9 | |
| | 3 | 5.2 | |
| | 4 | 4.9 | |
| | 5 | 4.1 | |
| | 6 | 4.5 | |
| UUO + PBS | 1 | 30.4 | 25.2 |
| | 2 | 25.0 | |
| | 3 | 24.6 | |
| | 4 | 23.0 | |
| | 5 | 19.6 | |
| | 6 | 28.7 | |
| UUO + control anti-miR | 1 | 24.8 | 21.6 |
| | 2 | 24.1 | |
| | 3 | 24.1 | |
| | 4 | 17.4 | |
| | 5 | 17.0 | |
| | 6 | 21.9 | |
| UUO + anti-miR-214 | 1 | 17.8 | 12.8 |
| | 2 | 14.6 | |
| | 3 | 17.9 | |
| | 4 | 10.6 | |
| | 5 | 12.3 | |

Anti-miR targeting miR-214 was also tested in a dose response experiment. Anti-miR was administered at Day −4, Day −1, and Day 3 of the study. Treatment groups included: (1) sham surgery, in which the ureter is exposed and manipulated, but not ligated; (2) UUO surgery treated with PBS; (3) UUO surgery treated with 20 mg/kg control anti-miR; (4) UUO surgery treated with 5 mg/kg anti-miR-214-1; (5) UUO surgery treated with 10 mg/kg anti-miR-214-1; (6) UUO surgery treated with 20 mg/kg.

Measurement of hydroxyproline content revealed a significant reduction in mice that underwent UUO surgery and received anti-miR-214-1, compared to mice that underwent UUO surgery and received control anti-miR (Table 12).

TABLE 12

Effect of dose-dependent inhibition of miR-214 in the UUO model on hydroxyproline content

| Groups | Dose (mg/kg) | Animal# | Hydroxyproline (µg/mg dry tissue) | Average content |
|---|---|---|---|---|
| Sham | — | 1 | 2.2 | 2.2 |
| | | 2 | 2.1 | |
| | | 3 | 2.3 | |
| | | 4 | 2.2 | |
| | | 5 | 2.1 | |
| | | 6 | 2.2 | |
| | | 7 | 2.1 | |
| | | 8 | 2.4 | |
| UUO + PBS | — | 1 | 8.3 | 7.7 |
| | | 2 | 6.9 | |
| | | 3 | 8.0 | |
| | | 4 | 6.1 | |
| | | 5 | 9.5 | |
| | | 6 | 7.1 | |
| | | 7 | 7.4 | |
| | | 8 | 8.7 | |
| UUO + control anti-miR | 20 | 1 | 7.6 | 7.7 |
| | | 2 | 8.6 | |
| | | 3 | 8.7 | |
| | | 4 | 7.9 | |
| | | 5 | 7.4 | |
| | | 6 | 7.8 | |
| | | 7 | 8.5 | |
| | | 8 | 5.3 | |
| UUO + anti-miR-214 | 5 | 1 | 6.2 | 6.5 |
| | | 2 | 7.5 | |
| | | 3 | 7.6 | |
| | | 4 | 6.3 | |
| | | 5 | 7.3 | |
| | | 6 | 5.7 | |
| | | 7 | 5.5 | |
| | | 8 | 5.6 | |
| | 10 | 1 | 6.5 | 6.3 |
| | | 2 | 6.6 | |
| | | 3 | 4.8 | |
| | | 4 | 5.8 | |
| | | 5 | 7.3 | |
| | | 6 | 6.1 | |
| | | 7 | 7.4 | |
| | | 8 | 6.1 | |
| | 20 | 1 | 3.1 | 6.2 |
| | | 2 | 6.1 | |
| | | 3 | 7.4 | |
| | | 4 | 7.0 | |
| | | 5 | 5.4 | |
| | | 6 | 7.5 | |
| | | 7 | 7.2 | |
| | | 8 | 6.4 | |

Collagen content was quantified by pico-sirius red staining (Table 13). The increase in collagen content is a measure of fibrosis and was observed to be reduced after anti-miR-214 treatment.

TABLE 13

Effect of dose-dependent inhibition of miR-214 in the UUO model on collagen content

| Groups | Dose (mg/kg) | Section# | Collagen area fraction (%) | Average content |
|---|---|---|---|---|
| Sham | — | 1 | 0.3 | 0.21 |
| | | 2 | 0.12 | |
| | | 3 | 0.24 | |
| | | 4 | 0.1 | |
| | | 5 | 0.41 | |
| | | 6 | 0.1 | |
| UUO + PBS | — | 1 | 1.12 | 1.23 |
| | | 2 | 1.63 | |
| | | 3 | 2.27 | |

TABLE 13-continued

Effect of dose-dependent inhibition of miR-214 in the UUO model on collagen content

| Groups | Dose (mg/kg) | Section# | Collagen area fraction (%) | Average content |
|---|---|---|---|---|
| | | 4 | 0.62 | |
| | | 5 | 0.88 | |
| | | 6 | 0.76 | |
| UUO + control anti-miR | 20 | 1 | 1.13 | 1.32 |
| | | 2 | 2.45 | |
| | | 3 | 1.15 | |
| | | 4 | 0.79 | |
| | | 5 | 1.16 | |
| | | 6 | 1.24 | |
| UUO + anti-miR-214 | 5 | 1 | 0.91 | 0.79 |
| | | 2 | 1.08 | |
| | | 3 | 0.63 | |
| | | 4 | 0.74 | |
| | | 5 | 0.63 | |
| | | 6 | 0.75 | |
| UUO + anti-miR-214 | 10 | 1 | 0.92 | 0.80 |
| | | 2 | 0.79 | |
| | | 3 | 0.84 | |
| | | 4 | 0.67 | |
| | | 5 | 0.76 | |
| | | 6 | 0.85 | |
| UUO + anti-miR-214 | 20 | 1 | 0.54 | 0.44 |
| | | 2 | 0.33 | |
| | | 3 | 0.39 | |
| | | 4 | 0.51 | |
| | | 5 | 0.57 | |
| | | 6 | 0.33 | |

FIG. 1 shows the results of a meta-analysis of the effect of anti-miR-214-1 on (A) collagen content and (B) hydroxyproline content in the kidneys of mice that underwent UUO surgery. Each data point represents an independent study containing 7 to 8 animals per group. The % normalization is calculated as follows:

% normalization=((1−treated−baseline)/(induced−baseline))*100, which can also be expressed as:

% normalization=((induced−treated)/(induced−baseline))*100, where "treated" is the collagen or hydroxyproline content in mice that underwent UUO surgery and were administered anti-miR-214-1; "baseline" is the collagen or hydroxyproline content in mice that underwent sham surgery; and "induced" is the collagen or hydroxyproline content in mice that underwent UUO surgery and were administered PBS. As shown in FIG. 1, administration of anti-miR-214 reduced collagen content (p=0.005) and hydroxyproline content (p=0.04) relative to negative controls.

Example 3

MiR-214 Expression in Murine Liver Fibrosis Samples

Administration of carbon tetrachloride ($CCl_4$) is an established experimental method for induction of liver fibrosis in mice (Natsume, M. et al., J. Leukoc. Biol. 1999, 66: 601-608) and thus is used as an experimental model that is reflective of human liver disease. Carbon tetrachloride was administered intraperitoneally either in a single dose or in multiple doses delivered over a period of time.

In case of the single dose study, 1.75 mL/kg of $CCl_4$ was administered via oral gavage to 10 male BALB/c mice (Taconic Farms). On day 3 and 7 after administration, five of the mice were euthanized, liver harvested and miR-214 levels were quantified by RT-PCR analysis. It was found that miR-214 was upregulated approximately 8-10 fold compared to normal liver (Table 14).

TABLE 14

Effect of liver fibrosis induced by a single dose of $CCl_4$ on miR-214 upregulation (%)

| Days after $CCl_4$ administration | (%) upregulation |
|---|---|
| 3 | +763 |
| 7 | +1020 |

In case of the multiple dose study, groups of BALB/c mice were administered intraperitoneally with either 100 μL of $CCl_4$ in mineral oil (20:80 $CCl_4$: mineral oil) or 100 μL of mineral oil only twice a week for a total of 7 doses. Livers were harvested 3 days after the last dose and miR-214 levels were quantified by a miR-214 microRNA detection kit (Applied Biosystems Inc). It was found that miR-214 was upregulated approximately 8-fold compared to normal liver.

Example 4

Efficient Delivery of Anti-MiR-214 to the Kidney

Anti-miR targeting miR-214 was evaluated in the UUO model of kidney fibrosis. In this study, the anti-miR used was anti-miR-214-1, which is a modified oligonucleotide consisting of 22 linked nucleosides; has the nucleobase sequence of SEQ ID NO: 3; nucleosides 1, 2, 12, 13, 14, 21, and 22 are 2'-O-methoxyethyl nucleosides; nucleosides 3 through 11 and 15 through 20 are 2'-fluoro nucleosides; each internucleoside linkage is a phosphorothioate linkage; and the cytosine at position 2 is a 5-methylcytosine (herein referred to as anti-miR-214-1). The control anti-miR used was a modified oligonucleotide consisting of X linked nucleosides, nucleosides 1, 2, 12, 13, 14, 21, and 22 are 2'-O-methoxyethyl nucleosides; nucleosides 3 through 11 and 15 through 20 are 2'-fluoro nucleosides; each internucleoside linkage is a phosphorothioate linkage; and the cytosine at position 2 is a 5-methylcytosine (herein referred to as control anti-miR).

In one experiment, anti-miR was administered at Day −11, Day −7, and Day −4 of the study. Treatment groups included: (1) sham surgery, in which the ureter is exposed and manipulated, but not ligated; (2) UUO surgery treated with PBS; (3) UUO surgery treated with 20 mg/kg control anti-miR; (4) UUO surgery treated with 20 mg/kg anti-miR-214-1. PBS or anti-miR was administered intraperitoneally at Day 11, Day 7 and Day 4 prior to UUO surgery. The day of UUO or sham surgery was Day 0. Kidney tissue was harvested from all groups on Day 3 following surgery. miR-214 levels were quantified by a miR-214 microRNA detection kit (Applied Biosystems Inc).

TABLE 15 miR-214 fold-change (%) compared to PBS control on delivery of anti-miR-214 to the kidney

| Group | (%) change |
|---|---|
| UUO + PBS | +325 |
| UUO + control anti-miR | +198 |
| UUO + anti-miR-214-1 | −100 |

Example 5

Inhibition of MiR-214 in Model of Ischemia/Reperfusion Injury

A model of ischemia reperfusion injury (IRI) is created in the mouse through unilateral or bilateral clamping of kidney arteries, which leads to tubule damage, inflammation, and fibrosis. Kidney dysfunction can occur either early (<5 days) or late (>7 days) in this model, with the early time points useful to test candidate agents for the treatment of acute kidney injury, and the later time points useful to model chronic fibrosis.

Anti-miR-214-1 was tested in the unilateral IRI model. Unilateral IRI was induced for a period of 30 minutes. Treatment groups were as follows: sham IRI procedure with PBS administered intraperitoneally; IRI with PBS administered intraperitoneally; IRI with anti-miR-214-1 administered intraperitoneally at a dose of 20 mg/kg; IRI with control anti-miR administered intraperitoneally at a dose of 20 mg/kg. PBS or anti-miR was administered on days 5, 6, and 7 following IRI, and animals were sacrificed 14 days after IRI. Kidney tissue was collected for analysis of collagen 1A1 and collagen 3A1 expression by quantitative RT-PCR. For this experiment, the control anti-miR used was a modified oligonucleotide consisting of 22 linked nucleosides, nucleosides 1, 2, 12, 13, 14, 21, and 22 are 2'-O-methoxyethyl nucleosides; nucleosides 3 through 11 and 15 through 20 are 2'-fluoro nucleosides; each internucleoside linkage is a phosphorothioate linkage; and the cytosine at position 2 is a 5-methylcytosine (referred to as control anti-miR).

Measurement of collagen 1A1 and collagen 3A1 revealed a significant reduction in both collagens in mice that underwent IRI and received anti-miR-214-1, compared to mice that underwent IRI and received control anti-miR (Table 16).

TABLE 16

Anti-miR-214 reduces collagen expression in the IRI model

| Groups | Animal # | Collagen 1A1 (Normalized Expression) | Mean | Collagen 1A1 (Normalized Expression) | Mean |
|---|---|---|---|---|---|
| Sham | 1 | 1.04 | 1.07 | 0.98 | 1.06 |
|  | 2 | 0.82 |  | 0.95 |  |
|  | 3 | 0.67 |  | 0.65 |  |
|  | 4 | 1.76 |  | 1.65 |  |
| 1R1-PBS | 1 | 29.20 | 44.15 | 29.71 | 47.08 |
|  | 2 | 73.34 |  | 69.43 |  |
|  | 3 | 49.94 |  | 58.21 |  |
|  | 4 | 52.77 |  | 61.80 |  |
|  | 5 | 30.21 |  | 33.45 |  |
|  | 6 | 51.47 |  | 63.83 |  |
|  | 7 | 38.13 |  | 40.15 |  |
|  | 8 | 41.36 |  | 39.19 |  |
|  | 9 | 21.29 |  | 21.50 |  |
|  | 10 | 42.92 |  | 46.55 |  |
|  | 11 | 54.96 |  | 54.05 |  |
| IRI-anti-miR-214 | 1 | 30.12 | 30.30 | 28.77 | 32.57 |
|  | 2 | 41.03 |  | 44.88 |  |
|  | 3 | 31.22 |  | 32.10 |  |
|  | 4 | 17.85 |  | 20.71 |  |
|  | 5 | 24.49 |  | 22.27 |  |
|  | 6 | 36.33 |  | 41.05 |  |
|  | 7 | 31.02 |  | 38.23 |  |
| IRI-control anti-miR | 1 | 47.99 | 43.53 | 49.68 | 45.43 |
|  | 2 | 30.01 |  | 26.22 |  |
|  | 3 | 55.31 |  | 55.82 |  |
|  | 4 | 53.41 |  | 48.12 |  |
|  | 5 | 44.07 |  | 56.29 |  |
|  | 6 | 33.36 |  | 40.16 |  |
|  | 7 | 40.55 |  | 41.70 |  |

Collagen content was quantitated by pico-sirius red staining (Table 17). The increase in collagen content is a measure of fibrosis and was observed to be reduced after anti-miR-214 treatment.

TABLE 17

Effect of inhibition of miR-214 in the IRI model on collagen content

| Groups | Animal # | Collagen area fraction (%) | Average content |
|---|---|---|---|
| Sham | 1 | 2.00 | 2.07 |
|  | 2 | 2.49 |  |
|  | 3 | 1.84 |  |
|  | 4 | 1.96 |  |
| IRI-PBS | 1 | 18.53 | 17.73 |
|  | 2 | 25.91 |  |
|  | 3 | 17.54 |  |
|  | 4 | 16.27 |  |
|  | 5 | 19.57 |  |
|  | 6 | 18.23 |  |
|  | 7 | 20.53 |  |
|  | 8 | 13.17 |  |
|  | 9 | 16.72 |  |
|  | 10 | 10.80 |  |
| UUO + control anti-miR | 1 | 13.80 | 15.27 |
|  | 2 | 14.10 |  |
|  | 3 | 13.29 |  |
|  | 4 | 15.85 |  |
|  | 5 | 14.94 |  |
|  | 6 | 18.43 |  |
|  | 7 | 16.63 |  |
|  | 8 | 15.11 |  |
| UUO + anti-miR-214 | 1 | 7.73 | 10.52 |
|  | 2 | 8.17 |  |
|  | 3 | 6.93 |  |
|  | 4 | 13.50 |  |
|  | 5 | 12.65 |  |
|  | 6 | 16.35 |  |
|  | 7 | 10.68 |  |
|  | 8 | 8.18 |  |

Example 6

MiR-214 Expression in Renal Epithelial Cells and Attenuation of TGF-β-Induced Collagen 1A1 Upregulation by Inhibition of MiR-214

TGF-β can stimulate epithelial-to-mesenchymal (EMT) transition in renal epithelial cells. EMT is characterized by a loss of cell adhesion and an increase in type I collagen production. Further, EMT has been implicated in kidney, lung, and possibly liver fibrosis. See, e.g., Kalluri et al., *J. Clin. Invest.* 112; 1776-84 (2003). The effect of TGF-β induced EMT on miR-214 levels in renal cells was therefore investigated. Primary renal epithelial cells (Lonza, Walkersville, Md.) were seeded at $1.5 \times 10^5$ cells per well in 6-well plates. Cells were either untreated, or treated with 10 ng/ml TGF-β for 24, 48, or 72 hours. Each condition was carried out in triplicate. MiR-214 levels were determined by RT-qPCR and normalized to U6 snRNA (Table 18). MiR-214 was upregulated in renal epithelial cells treated with TGF-β.

TABLE 18

Effect of TGF-β induction on miR-214 levels in renal epithelial cells

| | Average fold change miR-214 level relative to 0 h | |
|---|---|---|
| | −TGF-β | +TGF-β |
| 0 h | 1 | n.d. |
| 24 h | 1.90 | 1.53 |

To determine whether miR-214 knockdown can inhibit type I collagen formation in TGF-β induced EMT, renal epithelial cells stimulated with TGF-β were treated with anti-miR-214. Primary renal epithelial cells (Lonza, Walkersviile, Md.) were seeded at $1.5 \times 10^5$ cells per well in 6-well plates. Cells were untreated, treated with 10 ng/ml TGF-β, treated with 10 ng/ml TGF-β and 10 nM or 40 nM of an anti-miR-214 compound, or treated with 10 ng/ml TGF-β and 10 nM or 40 nM anti-miR-122 as a control. The cells were transfected overnight, and then treated with TGF-β for 48 hours. Each condition was carried out in triplicate. Collagen 1A1 levels were determined by RT-qPCR and normalized to GAPDH (Table 19). Col1A1 was upregulated by TGF-β treatment, which upregulation was attenuated by anti-miR-214 treatment.

TABLE 19

Effect of TGF-β induction on miR-214 levels in renal epithelial cells

| | Col1A1 fold-change relative to mock |
|---|---|
| mock | 1 |
| Mock + TGF-β | 2.47 |
| TGF-β + 10 nM anti-miR-214 | 1.63 |
| TGF-β + 40 nM anti-miR-214 | 0.87 |
| TGF-β + 10 nM anti-miR-122 | 2.34 |
| TGF-β + 40 nM anti-miR-122 | 2.04 |

Example 7

MiR-214 Expression in Human Idiopathic Pulmonary Fibrosis and a Mouse Model of Pulmonary Fibrosis To determine miR-214 expression in normal human lung samples and human idiopathic pulmonary fibrosis (IPF) samples. RNA was extracted from homogenized lung tissue using a miRNeasy kit (Qiagen, Valencia, Calif.). The amount of miR-214 in the lung RNA samples was determined by RT-qPCR, normalized to RNU19, and expressed as a fold-change relative to normal lung (Table 20). MiR-214 was found to be upregulated in lung tissue of patients with IPF.

TABLE 20

Upregulation of miR-214 in idiopathic pulmonary fibrosis

| Normal lung samples | Average | IPF samples: fold change | Average fold change |
|---|---|---|---|
| 0.85 | 1.12 | 0.21 | 3.08 |
| 1398 | | 5.21 | |
| 0.47 | | 1.47 | |
| 0.68 | | 3.90 | |
| 1.59 | | 3.75 | |
| 1.17 | | 3.92 | |

Bleomycin is a cytostatic drug commonly used in the treatment of cancer. As a side effect of its therapeutic use, in some patients bleomycin induces chronic pulmonary inflammation that may progress to fibrosis. Bleomycin-induced pulmonary fibrosis is easily reproduced in different species of mammals (e.g., mouse, rat, dog and pig), and as such experimental models using the drug are frequently used to investigate the cellular and molecular basis of lung interstitial fibrosis or to evaluate the ability of experimental compounds to prevent or treat pulmonary fibrosis. The upregulation of miR-214 was studied in the bleomycin-induced pulmonary fibrosis model.

The study was 14 days in length. Twelve C57BL/6 mice were each given a single intratracheal administration of bleomycin sourced from Hospira Inc. (1 unit/kg) on Day 1 of the study. Four C57BL/6 mice received only saline treatment. On day 3 after bleomycin or saline treatment, the saline-treated mice and four of the bleomycin-treated mice were sacrificed and the lungs removed. On day 7, four of the bleomycin-treated mice were sacrificed and the lungs removed, and on day 14, the last four bleomycin-treated mice were sacrificed and the lungs removed. RNA was extracted from homogenized lung tissue using a miRNeasy kit (Qiagen, Valencia, Calif.). The amount of miR-214 in the lung RNA samples was determined by RT-qPCR, normalized to Sno234 (a housekeeping small RNA), and expressed as a fold-change relative to saline-treated mice (Table 21). MiR-214 was upregulated in the bleomycin pulmonary fibrosis model.

TABLE 21

Upregulation of miR-214 in the bleomycin pulmonary fibrosis model

| | | miR-214 fold-change | |
|---|---|---|---|
| Treatment | Animal # | Fold-change (relative to saline) | Average |
| Saline day 3 | 1 | 0.99 | 1.00 |
| | 2 | 0.99 | |
| | 3 | 1.16 | |
| | 4 | 0.88 | |
| Bleomycin day 3 | 1 | 1.06 | 1.02 |
| | 2 | 1.05 | |
| | 3 | 1.02 | |
| | 4 | 0.96 | |
| Bleomycin day 7 | 1 | 1.47 | 1.59 |
| | 2 | 2.06 | |
| | 3 | 1.44 | |
| | 4 | 1.40 | |
| Bleomycin day 14 | 1 | 2.25 | 1.98 |
| | 2 | 1.49 | |
| | 3 | 2.42 | |
| | 4 | 1.76 | |

Example 8

Inhibition of MiR-214 in a Model of Pulmonary Fibrosis

To evaluate the effects of miR-214 inhibition on pulmonary fibrosis, anti-miR-214 was tested in the bleomycin-induced model of pulmonary fibrosis.

The study was 14 days in length. Three groups of 10 C57BL/6 mice each were given a single intratracheal administration of bleomycin sourced from Hospira Inc. (1 unit/Kg) on Day 1 of the study. Mice were then given intratracheal administration of saline, or anti-miR-214-1 (10 mg/kg) or control anti-miR (10 mg/kg) on Days 5, 6, and 7 of the study. A fourth group of mice received only saline treatment. On Day 14, mice were sacrificed and the lungs were removed.

From each group, four lungs were fixed and stained with Sirius Red for histological examination, while the remaining six lungs were processed to determine hydroxyproline content or fibrotic gene expression. Fibrotic gene expression (for example, Col1A1) was measured by real-time PCR performed on RNA isolated from the lungs.

TABLE 22

Effect of inhibition of miR-214 on collagen levels in the bleomycin pulmonary fibrosis model

| Treatment | Col1A1 mRNA Per lung sample | Average |
|---|---|---|
| Saline | 0.96 | 1.07 |
|  | 1.13 |  |
|  | 0.80 |  |
|  | 0.77 |  |
|  | 0.75 |  |
| Bleomycin + Saline | 1.99 | 2.3 |
|  | 2.10 |  |
|  | 3.42 |  |
|  | 1.92 |  |
|  | 1.95 |  |
| Bleomycin + anti-miR-214-1 | 2.42 | 1.16 |
|  | 2.03 |  |
|  | 0.98 |  |
|  | 1.55 |  |
|  | 1.60 |  |
|  | 0.62 |  |
| Bleomycin + control anti-miR- | 1.04 | 1.84 |
|  | 1.96 |  |
|  | 1.81 |  |
|  | 1.71 |  |

Col1A1, a collagen gene induced during fibrosis, was measured at the RNA level. Relative to saline, treatment with bleomycin induced a 2.3 fold increase in Col1A1 mRNA. Treatment with bleomycin followed by anti-miR-214-1 resulted significantly less Col1A1 expression relative to the bleomycin treatment. Accordingly, anti-miRs targeting miR-214 are useful for the treatment of pulmonary fibrosis.

What is claimed is:

1. A method of treating, preventing, or delaying the onset of fibrosis comprising administering to a subject having fibrosis or at risk for developing fibrosis a compound comprising a modified oligonucleotide consisting of 8 to 25 linked nucleosides, and having a nucleobase sequence at least 90% complementary to the nucleobase sequence of miR-214.

2. The method of claim 1 comprising selecting a subject having fibrosis.

3. The method of claim 1 comprising selecting a subject at risk for developing fibrosis.

4. The method of claim 1, wherein the fibrosis is kidney fibrosis, liver fibrosis, cardiac fibrosis, pulmonary fibrosis, restenosis-related vascular fibrosis, spleen fibrosis, age-related fibrosis, skin fibrosis, or post-transplantation fibrosis.

5. The method of claim 4, wherein the kidney fibrosis results from one or more of tubulointerstitial fibrosis, IgA nephropathy, interstitial fibrosis/tubular atrophy; chronic kidney damage, glomerular disease, glomerulonephritis, diabetes mellitus, idiopathy focal segmental glomerulosclerosis, membranous nephropathy, collapsing glomerulopathy, chronic recurrent kidney infection, end stage renal disease, acute kidney injury, chronic kidney injury, surgery, chemotherapy, radiation treatment, allograft rejection, chronic transplant rejection, or acute transplant rejection.

6. The method of claim 4 wherein the liver fibrosis is present in a subject having a disease selected from chronic liver injury, hepatitis infection, non-alcoholic steatohepatitis, and cirrhosis.

7. The method of claim 1 wherein the administering:
a) prevents progression of the fibrosis
b) delays the progression of the fibrosis; and/or;
c) reduces the fibrosis.

8. The method of claim 1 comprising administering at least one additional therapeutic agent.

9. The method of claim 8 wherein the at least one additional therapeutic agent is selected from anti-inflammatory agent, an immunosuppressive agent, an anti-diabetic agent, digoxin, a vasodilator, an angiotensin II converting enzyme (ACE) inhibitors, an angiotensin II receptor blockers (ARB), a calcium channel blocker, an isosorbide dinitrate, a hydralazine, a nitrate, a hydralazine, a beta-blocker, a natriuretic peptides, a heparinoid, and a connective tissue growth factor inhibitor.

10. The method of claim 1, wherein the compound consists of the modified oligonucleotide.

11. The method of claim 1, wherein the nucleobase sequence of the modified oligonucleotide is at least 95% or is 100% complementary to a nucleobase sequence selected from SEQ ID NO: 1 and 2.

12. The method of claim 1, wherein each internucleoside linkage of the modified oligonucleotide is a modified internucleoside linkage, and wherein the modified internucleoside linkage is optionally a phosphorothioate internucleoside linkage.

13. The method of claim 1, wherein the modified oligonucleotide comprises at least one nucleoside comprising a modified sugar, wherein each modified sugar is independently selected from a 2'-O-methoxyethyl sugar, a 2'-fluoro sugar, 2'-O-methyl sugar, and a bicyclic sugar moiety.

14. The method of claim 1, wherein the modified oligonucleotide consists of 15 to 23 linked nucleosides.

* * * * *